United States Patent
Nielsen et al.

(10) Patent No.: US 6,936,158 B2
(45) Date of Patent: Aug. 30, 2005

(54) METHOD AND APPARATUS FOR MEASURING ACCUMULATED AND INSTANT RATE OF MATERIAL LOSS OR MATERIAL GAIN

(75) Inventors: Kaj V. Nielsen, Roskilde (DK); Lars V. Nielsen, Rødovre (DK)

(73) Assignee: Metricorr Aps, Rodovre (DK)

( * ) Notice: Subject to any disclaimer, the term of this patent is extended or adjusted under 35 U.S.C. 154(b) by 0 days.

(21) Appl. No.: 10/166,571

(22) Filed: Jun. 10, 2002

(65) Prior Publication Data

US 2003/0006148 A1 Jan. 9, 2003

Related U.S. Application Data

(63) Continuation of application No. PCT/DK00/00689, filed on Dec. 11, 2000.

(30) Foreign Application Priority Data

Dec. 10, 1999 (DK) .......................................... 1999 01772

(51) Int. Cl.[7] .............................................. G01N 17/04
(52) U.S. Cl. ................................ 205/775.5; 205/776.5; 204/404; 324/700; 324/721
(58) Field of Search .......................... 205/775.5, 776.5, 205/777; 204/404; 324/700, 721, 71.2; 73/86

(56) References Cited

U.S. PATENT DOCUMENTS

| | | | |
|---|---|---|---|
| 3,067,386 A | | 12/1962 | Freedman |
| 3,633,098 A | * | 1/1972 | Westlund ..................... 324/721 |
| 4,217,544 A | | 8/1980 | Schmidt |
| 4,338,563 A | * | 7/1982 | Rhoades et al. ............. 324/700 |
| 5,243,297 A | * | 9/1993 | Perkins et al. .............. 324/700 |
| 5,446,369 A | | 8/1995 | Byrne et al. |
| 5,627,749 A | * | 5/1997 | Waterman et al. ............. 702/6 |

* cited by examiner

*Primary Examiner*—Kaj K. Olsen
(74) *Attorney, Agent, or Firm*—Klein, O'Neill & Singh, LLP; Howard J. Klein

(57) ABSTRACT

The present invention relates to a method and an apparatus for measuring accumulated and instant rate of material loss or material gain of metal elements for the detection of metal deposition (material gain) caused for example during deposition of coatings used in plating processes and corrosion (material loss) caused for example in pipelines during transportation of hazardous media. The apparatus and the method provides means for measuring accumulated and instant rate of material loss or material gain by inserting a probe in a measurement environment causing a probe experience metal deposition or corrosion. Further the apparatus and the method provides means for performing a temperature independent measurement of accumulated and instant rate of material loss or material gain accomplished without use of a temperature sensor device.

16 Claims, 7 Drawing Sheets

METHOD AND APPARATUS FOR MEASURING ACCUMULATED AND INSTANT RATE OF MATERIAL LOSS OR MATERIAL GAIN

This is a continuation of Application No. PCT/DK00/00689 filed Dec. 11, 2000.

This invention relates to a method and an apparatus for measuring accumulated and instant rate of material loss or material gain of metal elements for the detection of metal deposition (material gain) caused for example during deposition of coatings used in plating processes and corrosion (material loss) caused for example in pipelines during transportation of hazardous media.

The state of the art provides several techniques for quantification of accumulated corrosion and instant corrosion rate as for example disclosed in British patent applications GB 2 081 904, GB 2 266 379 and GB 2 286 844, and American patents U.S. Pat. No. 4,019,133, U.S. Pat. No. 5,069,774 and U.S. Pat. No. 5,217,596 which patents hereby are incorporated by reference. Generally, instant corrosion rates are determined by applying electrochemical techniques such as electrochemical impedance spectroscopy (EIS), linear polarisation resistance (LPR) or electrochemical noise (EN) measurements. However, since these techniques require a conducting electrolyte system e.g. a stable water phase they are not applicable in a corrosion process when water is not continuously present. Further, even though the requirements for performing electrochemical measurements are present inaccurate results may occur induced by additional current responses from redox-processes other than those involved in the particular corrosion process, which additional current responses may superimpose on the current response from the corrosion process and cause inaccurate or misleading results. In addition, the interpretation of the results of a measurement performed using one of the generally applied electrochemical techniques often require a specific expertise and knowledge of the user.

Accumulated corrosion is generally quantified by, weight loss measurements, ultra-sonic based thickness measurements, eddy-current techniques in near field and far field, magnetic flux leakage techniques or visual inspections (microscopy). In addition, a monitoring of accumulated corrosion in process plants commonly utilizes measurements of electrical resistance of a corroding metal wire placed in a probe (ER technique). All of the above mentioned techniques for determining accumulated corrosion generally require a series of measurements to be performed with regular time intervals (years, months, weeks or days) after which the individual measurements may be compared and translated into a degree of accumulated corrosion. None of the techniques provide a fast measurement of instant rate of corrosion or in other words the resolution of these techniques is insufficient. However, thin metal plates have been incorporated in commercial ER-probes and applied in process plants to follow the efficiency of corrosion inhibitor dosage with a fairly quick response (days, weeks or months depending on the actual corrosion rate).

The electrical resistance (ER) technique often utilizes a Wheatstone bridge circuit for the comparison of the electrical resistance of a test section or coupon exposed to a hostile environment and the electrical resistance of a reference coupon protected against the hostile environment. By repeating measurement at regular time intervals, e.g. on a weekly or monthly basis, the accumulated corrosion may be followed throughout time. To achieve acceptable results from a series of measurements reflecting the degree of accumulated corrosion, the applied ER-technique must measure the resistance of the test coupon and the resistance of the reference coupon accurately. However, the resistance of the test coupon and the resistance of the reference coupon are highly temperature dependent. Consequently, the effect of temperature variations from one measurement to another will cause unwanted inaccuracies in the measurements and decreases the comparability of the individual measurements included in a series of measurements.

Previous efforts in establishing temperature compensation has been achieved by incorporating a temperature sensor device mounted in the measurement environment for example mounted on the test coupon and performing temperature compensation in accordance with the data presented by the temperature device. However this kind of temperature compensation obviously introduces further inaccuracies in the measurement since the temperature characteristics of the temperature sensor device are not identical to the temperature characteristics of the test coupon or the reference coupon.

An object of the present invention is to provide an apparatus and a method for measuring accumulated and instant rate of material loss or material gain by inserting a probe in a measurement environment causing the probe to experience metal deposition or corrosion.

A particular advantage of the present invention is the provision of a temperature independent measurement of accumulated and instant rate of material loss or material gain accomplished without use of a temperature sensor device.

A further advantage of the present invention is the provision of measurement and balancing of real and imaginary voltage components variations endured by a measuring probe.

A particular feature of the present invention is the provision of compatibility of the present invention to numerous probes having different physical attributes and having different physical dimensions.

The above object, the above advantage and the above feature together with numerous other objects, advantages and features which will be evident from the below detailed description of an embodiment of the present invention is according to a first aspect of the present invention obtained by an apparatus for measuring accumulated and instant rate of material loss or material gain and comprising:

(a) a DC supply supplying said apparatus with power to perform measuring operations and said DC supply defining a positive DC voltage and a negative DC voltage, (b) a metal element defining a coated section having a first connector, a non-coated section having a second connector, and an interface having a third connector, said interface providing electrical and thermal connection between said coated section and said non-coated section experiencing corrosion or metal deposition in a measurement environment, (c) a first input power system generating a first system input signal and generating a common input signal to said third connector of said metal element, (d) a first power transmitter amplifier having a first power transmitter input receiving said first system input signal and having a first power transmitter output generating a first excitation output signal, (e) a first resistor for interconnecting said first power transmitter output and said first connector of said coated section of said metal element so as to constitute a first path of said first excitation output signal from said first power transmitter output through said first resistor and said coated section of said metal element to said third connector of said metal element, said first excitation output signal inducing a first metal element voltage across said coated section of said metal element, (f) a second resistor for interconnecting said first power transmitter output and said second connector of said non-coated section of said metal element so as to constitute a second path of said first excitation output signal from said first power transmitter output through said second resistor and said non-coated section of said metal element to said third connector of said metal element, said first excitation output signal further inducing a second metal element voltage across said non-coated section of said metal element, and (g) a first sensor amplifier having a first sensor amplifier input connected to said first connector of said coated section of said metal element, having a second sensor amplifier input connected to said second connector of said non-coated section of said metal element, and having a first sensor output generating a first sensor amplifier output signal constituted by an amplification of said first metal element voltage, said second metal element voltage and/or a voltage difference between said second metal element voltage and said first metal element voltage, said metal element defining a first resistance between said first connector of said coated section and said third connector of said metal element and a second resistance between said second connector of said non-coated section and said third connector of said metal element, said second resistance increases as a function of corrosion and decreases as a function of metal deposition so as to induce said voltage difference between said second metal element voltage and said first metal element voltage.

According to the basic realisation of the first aspect of the present invention the voltage difference between the coated and non-coated section of the metal element or probe provides a measurement of accumulated corrosion, whereas the second resistance in conjunction with time related changes of the second resistance at one temperature provides a measurement of instant rate of material loss or material gain. The resistance of the metal element constituted by the first resistance and said second resistance of may be in a range from 4 $\mu\Omega$ to 4 K$\Omega$ such as ranges 4 m$\Omega$ to 400 m$\Omega$ or 10 m$\Omega$ to 100 m$\Omega$. The apparatus according to the first aspect of the invention provides the possibility to apply a wide variety of probes or metal elements for measuring accumulated or instant rate of material loss or material gain. This compatibility further ensures that the apparatus generates repeatable measurements irrespective of probe type.

The term metal element is a generic term for a probe and should be construed as a measurement unit providing a change according to environmental exposure. The metal element of the apparatus according to the first aspect of the present invention may define a cross section having any arbitrary shape such as a square, circular, elliptic, triangular, or a rectangular cross section or any combinations thereof, preferably the metal element defines a rectangular cross section. The metal element may further comprise any arbitrary metallic composition such as alloys Steel, Stainless Steel, Iron, Copper, or Aluminum or any combinations thereof or be constituted by a composite material comprising any of the metallic compositions. The physical dimensions or attributes of the metal element may be arbitrary, however, obviously the calculations needed for determining a change in thickness that being either positive or negative will become substantially simpler by applying metal elements having simple physical shapes and dimensions.

The interface between the coated and non-coated section of the metal element of the apparatus according to a first aspect of the invention may provide an electrical and a thermal connection between the coated section and the non-coated section constituted by an electrically and thermally conductive wire. Alternatively, the interface of the metal element may provide an electrical and a thermal connection between the coated section and the non-coated section constituted by positioning the coated section and the non-coated section in direct contact and adjacent to each other, or the interface may define a boundary between the coated section and the non-coated section of a metal element constituted by one metal piece or one composite metal piece. The configuration of the interface provides the possibility for changing or substituting the non-coated section of the metal element after or before a measurement of different environments.

The DC voltage supply of the apparatus according to the first aspect of the present invention supplies a DC voltage in the range +24V to −24V such as ranges +12V to −12V, +5V to −5V or combinations thereof, preferably the DC voltage supply supplies a positive DC voltage of +12V and a negative DC voltage of −12V.

The apparatus according to the first aspect of the present invention may further comprise (h) a first detector having a first detector input receiving the first sensor amplifier output signal from the first sensor amplifier output, performing a conversion of the first sensor amplifier output signal and generating a first detector output signal. The first detector provides a conversion of the measured and amplified voltage difference between the voltage across the non-coated section and the coated section of the metal element. The conversion provides the first detector output signal being computer treatable or compatible with communication to a calculation facility. Further the apparatus according to the first aspect of the present invention may comprise:

(i) a second input power system generating a second system input signal and generating said common input signal to said third connector of said metal element, (j) a second power transmitter amplifier having a second power transmitter input receiving a second system input signal and having a second power transmitter output generating a second excitation output, (k) a third resistor for interconnecting said second power transmitter output and said first connector of said coated section of said metal element so as to constitute a first path of said second excitation output signal from said second power transmitter output through said third resistor and said coated section of said metal element to said third connector of said metal element, said second excitation output signal inducing in corporation with said first excitation output signal said first metal element voltage across said coated section of said metal element, (l) a fourth resistor for interconnecting said second power transmitter output and said second connector of said non-coated section of said metal element so as to constitute a second path of said second excitation output signal from said second power transmitter output through said fourth resistor and said non-coated section of said metal element to said third connector of said metal element, said second excitation output signal further inducing in corporation with said first excitation output signal said second metal element voltage across said non-coated section of said metal element, (m) a second sensor amplifier having a third sensor amplifier input connected to said first connector of said coated section of said metal element, having a fourth sensor amplifier input connected to said third connector of said metal element, and having a second sensor amplifier output generating a second sensor output signal constituted by an amplification of said first metal element voltage, (n) a second detector having a second detector input receiving said second sensor output signal from said second sensor amplifier output, performing a conversion of said second sensor amplifier output, and generating a second detector output signal, and (o) a temperature compensating feedback circuit for compensating temperature induced variations in said first and second resistance of said metal element and utilizing said second detector output in controlling amplitude of said first system input signal and said second system input signal so as to decrease said first system input signal and said second system input signal when said first resistance increases and so as to increase said first system input signal and said second system input signal when said first resistance decreases.

The temperature compensating feedback circuit according to the first aspect of the present invention ensures that the temperature variations induced in the metal element are compensated so as to prevent erroneous measurements. The temperature compensating feedback circuit presents substantial advantages of the present invention in the provision of reliable and repeatable measurements of accumulated and instant rate of material loss or material gain. The second resistance of the metal element may be exposed to environmental temperature variations or self-induce temperature variations as excitation current is conducted through the metal element. These temperature variations may cause severe misinterpretations of the actual state of the environment being examined and therefore temperature compensation provides a significant improvement of the generally employed techniques for measuring accumulated material loss or material gain.

The temperature compensating feedback circuit may comprise:

(a) an oscillator providing a clock pulse signal, (b) a reference potentiometer connected to said DC supply voltage and generating a reference voltage output signal, (c) a comparator having an inverting comparator input connected to said second detector output, a non-inverting comparator input connected to said reference voltage output, and having a comparator output generating a comparator output signal constituted by a positive output voltage or a negative output voltage relative to polarity of voltage difference between said inverting comparator input and said non-inverting comparator input, (d) a counter having a counter clock input receiving said clock pulse signal, having a counter input receiving said comparator output signal, and having a digital counter output generating a counter output digital number, said counter output digital number being increased when receiving a clock pulse signal and receiving said comparator output signal having a positive output voltage, or said counter output digital number being reduced when receiving a clock pulse signal and receiving said comparator output signal having a negative output voltage, (e) a first digital ladder having a first digital input connected to said digital counter output and having a first analogue input receiving said first system input signal, said first digital ladder performing a conversion of said counter output digital number to a required amplitude of said first system input signal and generating said first system input signal having an amplitude in accordance with said counter output digital number, (f) a second digital ladder having a second digital input connected to said digital counter output and having a second analogue input receiving said second system input signal, said second digital ladder performing a conversion of said counter output digital number to said required amplitude of said second system input signal and generating said second system input signal having said amplitude in accordance with said counter output digital number.

The temperature compensating feedback circuit of the apparatus according to the first aspect of the present invention may further comprise:

(g) a discriminating circuit having a detector unit measuring said first system input signal and generating a DC detector output, and having a discriminator meter comparing said DC detector output with a fixed reference voltage defined by a voltage divider and said discriminator meter displaying a voltage difference defined between said DC detector output and said fixed reference voltage so as to provide balancing information of said apparatus and enable balancing by adjusting said reference potentiometer, or (g) a discriminating circuit having a detector unit measuring said second system input signal and generating a DC detector output, and having a discriminator meter comparing said DC detector output with a fixed reference voltage defined by a voltage divider and said discriminator meter displaying a voltage difference defined between said DC detector output and said fixed reference voltage so as to provide balancing information of said apparatus and enable balancing by adjusting said reference potentiometer.

The possibility for implementing the discriminating circuit measuring either the first or the second input signal enables for constructing the circuit in accordance with customized preferences.

The apparatus according to the first aspect of the present invention may provide the first system input signal and the second system input signal constituted by a DC voltage signal or an AC voltage signal. However, the first system input signal and the second system input signal are constituted by a square-wave voltage signal having a first frequency and a second frequency in the range 1 Hz to 100 KHz, such as ranges 50 Hz to 50 KHz, 500 Hz to 5 KHz or 1 KHz to 4 KHz. Preferably the first system input signal is constituted by a square-wave voltage signal having a first frequency of 1.5 KHz and the second system input signal is constituted by a square-wave voltage signal having a second frequency of 2.5 KHz. Additionally, the first power transmitter amplifier may provide the first excitation output signal constituted by a square-wave current signal having the first frequency and the second power transmitter amplifier may provide the second excitation output signal constituted by a square-wave current signal having the second frequency. The introduction of two excitation signals having two different frequencies enables the apparatus according to the first aspect of the present invention to perform a frequency selective measurement of the first metal element voltage and the voltage difference between the second metal element voltage and the first metal element voltage. Thus the first sensor amplifier may provide a frequency selective amplification of part of the first metal element voltage and the second metal element voltage constituted by the first frequency and the second sensor amplifier may provide a selective amplification of part of the first metal element voltage constituted by the second frequency. The apparatus utilizes these measurements partly to the end of temperature compensating the apparatus and partly to the end of performing regular measurements of the accumulated or instant rate of material loss or material gain.

The first resistor and the second resistor of the apparatus according to the first aspect of the present invention may be smaller than or equal to the first and second resistance of the metal element, or greater than the first and second resistance of the metal element, or greater by a factor in the range 10 to 100000 such as ranges 1000 to 10000 or 3000 to 6000. Similarly, the third resistor and the fourth resistor of the apparatus according to the first aspect of the present invention may be smaller than or equal to said first and second resistance of said metal element, or greater than said first and second resistance of said metal element, or greater by a factor in the range 10 to 100000 such as ranges 1000 to 10000 or 3000 to 6000. However preferably the third resistor and the fourth resistor are substantially coincidental with the first resistor and the second resistor. The first, second, third and fourth resistors being greater than the resistors of the metal element provides substantially equal excitation currents through the coated section and the non-coated section of the metal element.

The conversion of the first sensor amplifier output signal performed by the first detector of the apparatus according to the first aspect of the present invention may be constituted by converting the alternating first sensor amplifier output signal into a DC voltage signal in the range −24V to +24V such as ranges −12V to +12V, −5V to +5V or preferably the DC voltage signal constituting the first detector output signal is in the range −1V to +1V. Likewise the conversion of the second sensor output signal performed by the second detector may be constituted by converting the alternating second sensor output signal into a DC voltage signal in the range −24V to +24V such as ranges −12V to +12V, −5V to +5V or preferably the DC voltage signal constituting the first detector output signal is in the range 0V to +5V.

Balancing and impedance measuring units are further introduced in the apparatus according to the first aspect of the present invention so that the apparatus may further comprise:

(p) a first phase detective means connected to said first sensor amplifier output and performing a phase selective conversion of said first sensor amplifier output signal to a first real vector component voltage and a first imaginary vector component voltage of said voltage difference between said second metal element voltage and said first metal element voltage having said first frequency, (q) a third sensor amplifier having a fifth sensor amplifier input connected to said second connector of said non-coated section of said metal element, having a sixth sensor amplifier input connected to said third connector of said metal element, and having a third sensor amplifier output generating a third sensor output signal constituted by an amplification of said part of said second metal element voltage having said second frequency, (r) a second phase detective means connected to said third sensor amplifier output and performing a phase selective conversion of said third sensor amplifier output signal to second real vector component voltage and a second imaginary vector component voltage of said second metal element voltage having said second frequency, (s) a real vector component balancing circuit having a real vector component balancing circuit output generating a real balancing output signal and a real vector component balancing circuit input receiving said first system input signal, (t) a third power transmitter amplifier having third power transmitter input connected to said real vector component balancing circuit output and having a third power transmitter output connected to said first connector on said coated section of said metal element and generating a third power transmitter output signal for balancing of said first real vector component voltage, (u) an imaginary vector component balancing circuit having an imaginary vector component balancing circuit output generating an imaginary balancing output signal and an imaginary vector component balancing circuit input receiving said first system input signal phase shifted by 90° and 270°, and (v) a fourth power transmitter amplifier having fourth power transmitter input connected to said imaginary vector component balancing circuit output and having a fourth power transmitter output connected to said first connector on said coated section of said metal element and generating a fourth power transmitter output signal for balancing of said first imaginary vector component voltage.

The apparatus according to the first aspect of the invention further by implementation of balancing and impedance measuring units provides the means for complex measurements of accumulated and instant rate of material gain and material loss. The metal element may endure complex changes in material attributes, which may result in not only a real change but also an imaginary change. The terms real and imaginary in this context is to be construed as describing the two vector components of an impedance. The apparatus including all of the above-described features enable precise measurements applying a wide variety of metal elements even during long term measurement in harsh conditions such as temperature varying environment causing metal deposition or corrosion of the metal elements.

The above object, the above advantage and the above feature together with numerous other objects, advantages and features which will be evident from the below detailed description of an embodiment of the present invention is according to a second aspect of the present invention obtained by a method for measuring accumulated and instant rate of material loss or material gain and comprising:

(a) providing an apparatus comprising:
(i) a DC supply defining a positive DC voltage and a negative DC voltage,
(ii) a metal element defining a coated section having a first connector, a non-coated section having a second connector, and an interface having a third connector, said interface providing electrical and thermal connection between said coated section and said non-coated section and said non-coated section experiencing corrosion or metal deposition in a measurement environment,
(iii) an first input power system having a first power output,
(iv) a first power transmitter amplifier having a first power transmitter input receiving said first system input signal and having a first power transmitter output, (v) a first resistor for interconnecting said first power transmitter output and said first connector of said coated section of said metal element so as to constitute a first path of said first excitation output signal from said first power transmitter output through said first resistor and said coated section of said metal element to said third connector of said metal element, (vi) a second resistor for interconnecting said first power transmitter output and said second connector of said non-coated section of said metal element so as to constitute a second path of said first excitation output signal from said first power transmitter output through said second resistor and said non-coated section of said metal element to said third connector of said metal element, and (vii) a first sensor amplifier having a first sensor amplifier input connected to said first connector of said coated section of said metal element, having a second sensor amplifier input connected to said second connector of said non-coated section of said metal element, and having a first sensor output, (b) supplying said apparatus with power to perform measuring operations, (c) generating a first system input signal and generating a common input signal to said third connector of said metal element, (d) generating a first excitation output signal on said first power transmitter output, (e) inducing a first metal element voltage across said coated section of said metal element by means of said first excitation output signal, (f) inducing a second metal element voltage across said non-coated section of said metal element by means of said first excitation output signal further, (g) generating a first sensor amplifier output signal constituted by an amplification of said first metal element voltage, said second metal element voltage and/or a voltage difference between said second metal element voltage and said first metal element voltage by means of said first sensor output, and (h) defining a first resistance between said first connector of said coated section and said third connector of said metal element and a second resistance between said second connector of said non-coated section and said third connector of said metal element, said second resistance increases as a function of corrosion and decreases as a function of metal deposition so as to induce said voltage difference between said second metal element voltage and said first metal element voltage and to determine corrosion of or metal deposition of said metal element from said second resistance increase or decrease.

The method according to the second aspect of the present invention comprises application of the apparatus according to the first aspect of the present invention including any of the features as defined above.

DETAILED DESCRIPTION OF THE PRESENT INVENTION

In the following the apparatus for measuring accumulated corrosion and instant corrosion rate according to the present invention will be described in further detail.

Figure 1:
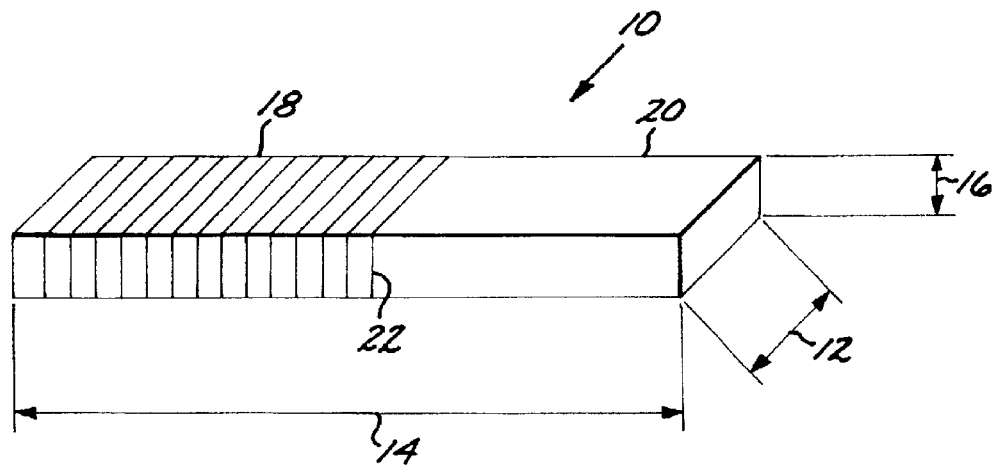
FIG. 1 shows a metal element used for measuring accumulated corrosion and instant corrosion rate.

FIG. 1 shows a metal element designated in its entirety by numeral 10, which metal element 10 comprises a first section 18 and a second section 20 joined at an interface 22. The first section 18 is coated with a protective layer so as to prevent the first section 18 of the metal element 10 to corrode or experience metal deposition. The second section 20 is not coated with a protective layer as the first section 18 and consequently the second section 20 of the metal element 10 will corrode or experience metal deposition when positioned in a hostile environment.

The metal element 10 may further have any arbitrary shape and/or comprise any arbitrary chemical composition. The metal element 10 may be constituted by for example a composite material. However, the metal element 10 defines a rectangular shape having width 12, length 14 and thickness 16, which in concurrence with resistivity of the metal element 10 and the temperature of the metal element 10 determines the total resistance of the metal element 10 in accordance with the equation:

$$R(T, W, L, \sigma) = \rho(T) \cdot \frac{L}{W \cdot \sigma}$$

where $R(T,L,W,\sigma)$ having variables temperature T, thickness $\sigma$ 16, width 12 and length 14 is the resistance of the metal element 10 over the length 14, $\rho(T)$ having variable temperature T is the resistivity of the metal element 10 material. Note however that the above equation is only applicable in determining the total resistance of the metal element 10 before the metal element 10 is placed in a hostile environment. Since the total resistance after the metal element 10 is placed in a hostile environment must be calculated as a series resistance of the second section 20 deteriorating or expanding in the hostile environment and the first section 18 unaffected in the hostile environment.

Figure 2:
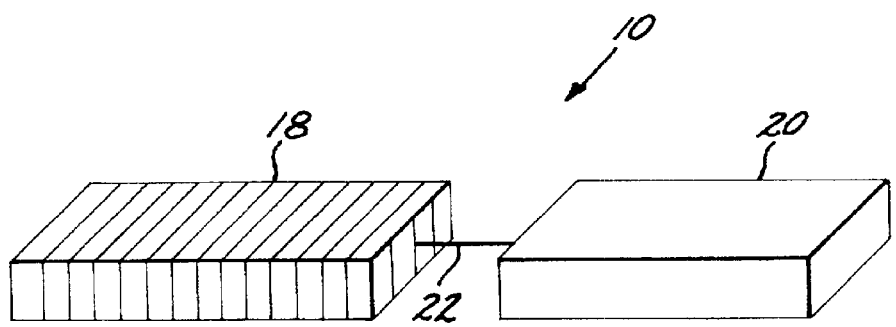
FIG. 2 shows a metal element constituted by two metal parts for measuring accumulated corrosion and instant corrosion rate.

Alternatively the first section 18 and the second section 20 of the metal element 10 may as shown in FIG. 2 in one alternative embodiment of the present invention be physically separated and connected there between by a conductive wire constituting the interface 22. Thus the first section 18 and the second section 20 constitutes a series connection.

The interface 22 may be constructed from any conducting or semi-conducting material providing a thermal connection as well as a electric connection between the first section 18 and the second section 20 of the metal element 10.

As the metal element 10 is inserted into a hostile environment then corrosion or metal deposition sets in on the non-coated part of the metal element 10, thus causing the second section 20 to alter characteristics. The corrosion of the second section 20 reduces the dimensions of the second section 20 and hence the resistance of the second section 20 increases relative to the resistance of the coated part of the first section 18 of the metal element 10. Whereas metal deposition on the second section 20 increases the dimensions of the second section 20 and hence the resistance of the second section 20 decreases relative to the resistance of the coated first section 18 of the metal element 10.

Figure 3:
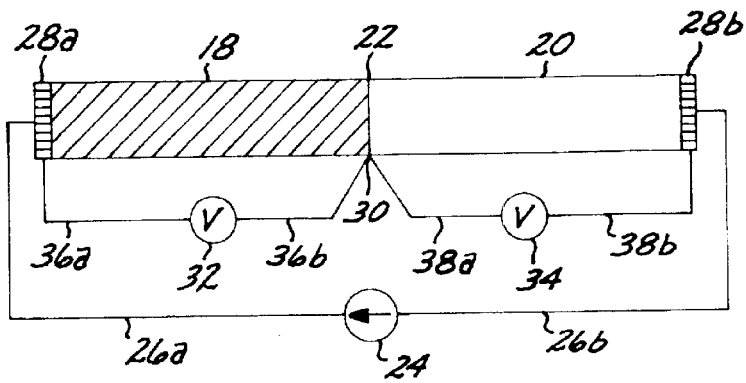
FIG. 3 shows a schematic diagram of a set-up for measuring accumulated corrosion using a metal element.

FIG. 3 shows a schematic set-up for measuring the accumulated corrosion by using the metal element 10 described above. Current generating means 24 apply a constant current through the first section 18 and second section 20 of the metal element 10 by applying the constant current to connections 26a and 26b connected to connectors 28a and 28b situated on the either side of the metal element 10. Thus the constant current is conducted from the first section 18 to the second section 20. Voltages between connectors 28a and 28b and a common connector 30 is measured through voltage sensitive means 32 and 34 connected to the connectors 28a and 28b and to the common connector 30 through connections 36a, 36b, 38a and 38b.

Figure 4:
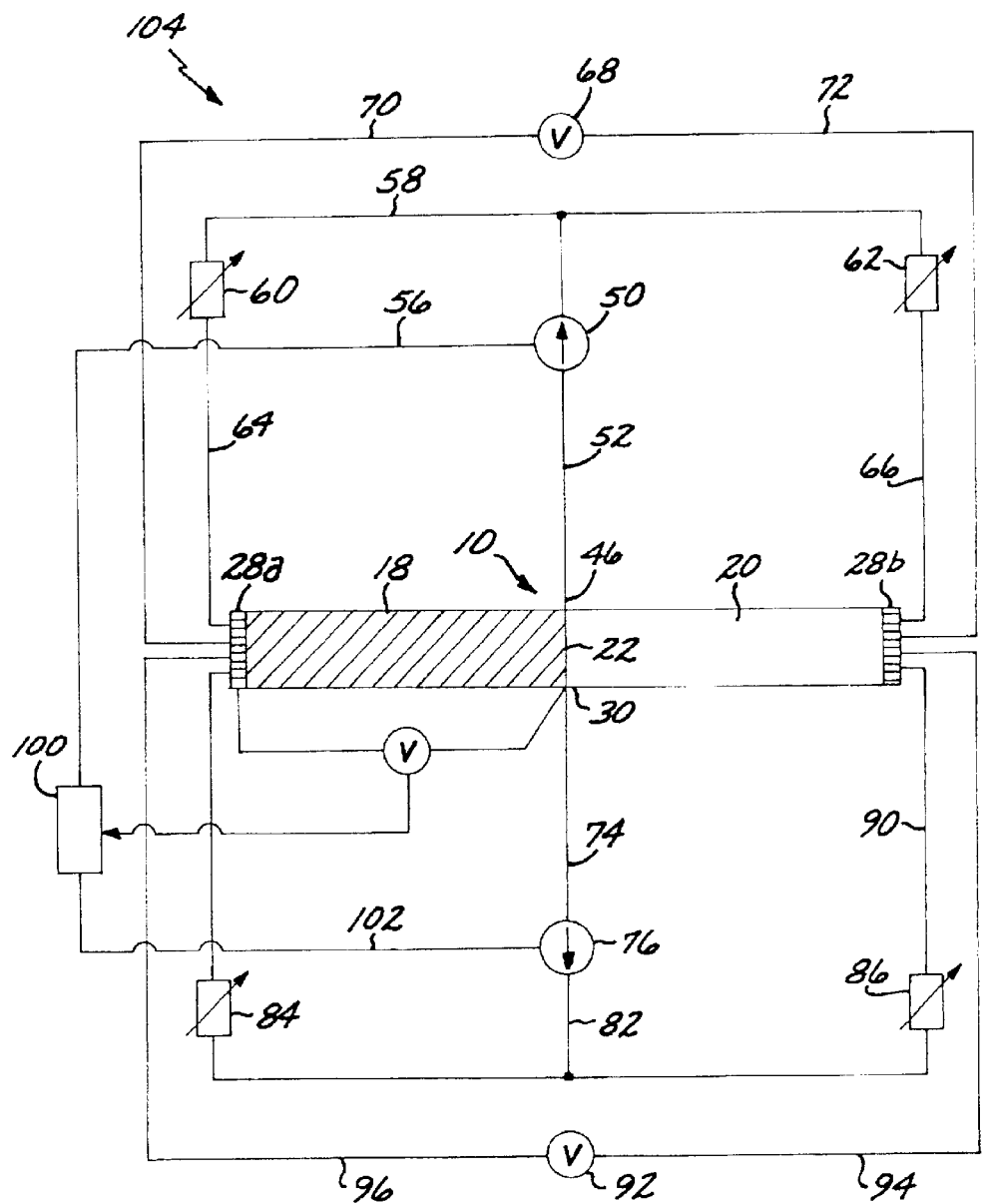
FIG. 4 shows a schematic block diagram of an apparatus for measuring accumulated and instant rate of material loss or material gain.

FIG. 4 shows a schematic block diagram of the apparatus for measuring accumulated and instant rate material loss or material gain according to the present invention. In the apparatus designated in its entirety by numeral 104 current is supplied to the metal element 10 by a first current generating means 50. The first current generating means 50 is connected through a connection 52 to a first center connector 40 placed substantially adjacent to or on the interface 22 between the first section 18 and the second section 20 and is connected through a branching connection 58 to a first balancing means 60 and 62. The first balancing means 60 and 62 schematically shown in FIG. 4 as being connected back to the metal element 10 through connections 64 and 66 connected to the connector 28a on the first section 18 of the metal element 10 and connected to the connector 28b on the second section 20 of the metal element 10. Thus the current generating means 50 provides current to two alternative current paths generally known as two sides of a bridge circuit.

The voltage difference dV defined as the difference between $V_C$ and $V_R$ between the connectors 28a and 28b is measured through connections 70 and 72 by a first sensing means 68 providing an output relating to both real and imaginary components of the and the voltage difference dV. The indices applied are defined as "C" for coupon or non-coated section of a metal element and "R" for reference or coated section of a metal element. The changes of the voltage $V_C$ relative to the voltage $V_R$ while the metal element 10 is exposed to a hostile environment, i.e the second section 20 of the metal element corroding or experiencing metal deposition since the second section 20 is not coated, provides data which may be used for the determination of the accumulated material loss or material gain. The differential voltage dV is defined by:

$$dV = V_C - V_R$$

$$dV = R_C(T,\sigma) \cdot I_C - R_R(T,\sigma) \cdot I_R$$

where $R_C(T,\sigma)$ is the resistance of the second section 20, $R_R(T,\sigma)$ is the resistance of the first section 18, $I_C$ and $I_R$ are the currents through $R_C$ and $R_R$ respectively.

The equation for determining the resistance of the first and second sections 18 and 20 of the metal element 10 provides the basis for traditional measurements of accumulated corrosion. The resistance $R_C$ of the second section 20 of the metal element 10 is measured at specific time intervals (typically weeks or months) and compared with measurements of the resistance $R_R$ of the first section 18 of the metal element 10, which resistance $R_C$ and $R_R$ only vary with the actual temperature existing at the time of measurement. Mathematical expressions based on the ratio between the resistance $R_C$ and the resistance $R_R$ or the difference between the resistance $R_C$ and the resistance $R_R$ are normally applied for assessments of the thickness σ 16 of the metal element 10 and hereby the thickness reduction of the second section 20, i.e. the degree of accumulated corrosion of the second section 20 of the metal element 10. Resolution of the thickness reduction in the order of 10–25 μm is quite common in the traditional measurements of accumulated corrosion.

The instant corrosion rate of the metal element 10 may be determined from below equation:

$$V_{corr} = -\frac{d\sigma'}{dt} = \frac{\frac{dR_C}{dt}}{\frac{dR_C}{d\sigma'}}$$

where $V_{corr}$ defines the instant corrosion rate of the metal element 10, σ' defines the thickness of the second section 20, dσ'/dt defines the rate of thickness change over time equal to $dR_C/dt$ defining rate of change of resistance $R_C$ over time divided by $dR_C/d\sigma'$ defining rate of change of resistance $R_C$ over change of thickness σ'.

By differentiating the resistance $R_C$ with respect to thickness σ' following result is obtained:

$$\frac{dR_C}{d\sigma'} = \frac{-\rho(T) \cdot \frac{L}{W}}{\sigma'^2} = \frac{-dR_C^2}{\rho(T) \cdot \frac{L}{W}}$$

By inserting the result for $dR_C/d\sigma'$ into equation for $V_{corr}$, it follows that the instant corrosion rate $V_{corr}$ of the metal element 10 may be expressed as:

$$V_{corr} = \frac{dR_C}{dt} \cdot \frac{\rho(T) \cdot L}{W \cdot R_C^2}$$

The instant corrosion rate $V_{corr}$ of the metal element 10 may be measured under constant temperature conditions by measuring co-ordinate values of the changes of resistance $dR_C$ over time dt, measuring the absolute value of the resistance $R_C$, and determining the specific resistivity ρ(T) of the metal element 10 material at temperature T.

Since the first section 18 of the metal element 10 is protected from corrosion or metal deposition, no change of the resistance $R_R$ occurs during constant temperature.

Accordingly, a change $\Delta dR_{C-R}$ in the resistance difference $dR_{C-R}$ defined between resistance $R_C$ of the metal element 10 and resistance $R_R$ of the metal element 10 is substantially equal to the change $dR_C$ of the resistance $R_C$ of the metal element 10 caused by corrosion or metal deposition:

$$\Delta dR_{C-R} = dR_C$$

and $$\frac{\Delta dR_{C-R}}{dt} = \frac{dR_C}{dt}$$

Thus a real time instant corrosion rate detection may be realized by measuring the difference $dR_{C-R}$ between resistance $R_C$ of the second section 20 of the metal element 10 and resistance $R_R$ of the first section 18 of the metal element 10 throughout time, and accordingly establish the differential coefficient $\Delta dR_{C-R}/dt$. The present invention is capable of measuring the required difference $dR_{C-R}$ between resistance $R_C$ and resistance $R_R$ as a function of time having a resolution in the order of a tenth of $\mu\Omega$.

The first current generating means 50 shown in FIG. 4 provides a DC, an AC, or preferably the first current generating means 50 generates a square-wave signal having a frequency in the range 1 Hz to 100 KHz, such as ranges 50 Hz to 50 KHz, 500 Hz to 5 KHz or 1 KHz to 4 KHz, however, preferably the frequency of the square-wave signal is 1.5 KHz.

Further in the apparatus 104 current is supplied to the metal element 10 by a second current generating means 76 having one terminal connected to the metal element 10. The second current generator 76 is connected through connection 74 to a second center connector 30 placed substantially adjacent to or on the interface 22 between the first section 18 and the second section 20 and is connected a branching connection 82 to a second balancing means 84 and 86. The second balancing means 84 and 86 are schematically shown in FIG. 4 as being connected back to the metal element 10 through connections 88 and 90 to the connector 28a on the first section 18 and to the connector 28b on the second section 20 of the metal element 10. Thus the second current generator 76 provides as the first current generator 50 current to two alternative current paths The second current generating means 76 applies a DC, an AC, or preferably the second current generating means 76 generates a square-wave signal having a frequency in the range 1 Hz to 100 KHz, such as ranges 50 Hz to 50 KHz, 500 Hz to 5 KHz or 1 KHz to 4 KHz, however, preferably the frequency of the AC current signal is 2.5 KHz.

The voltage $V_C$ between the connector 28a and the second center connector 30 is additionally measured through connections 36a and 36b by a second sensing means 32.

As current passes through the first section 18 and the second section 20 of the metal element 10 the temperature of the metal element 10 changes and hence the resistivity of the metal element material changes accordingly. Thus the resistance value of the first section 18 and the second section 20 varies not only as a function of the corrosion or metal deposition but varies also in accordance with the temperature the metal element 10 is exposed to and additionally in accordance with the self-induced temperature changes caused by applying an excitation current through the metal element 10. In order to prevent erroneous measurements caused by temperature effects the apparatus 104 comprises temperature compensating means 100. The voltage $V_R$ measured by the second sensing means 32 constitutes an input signal directed through a connection 98 to the temperature compensating means 100 which subsequently provides output feedback signals proportional to the input signal through a connections 56 and 102 to the first and second current generator 50 and 76.

Before the metal element 10 is placed in a hostile environment the first and second balancing means 60, 62, 84 and 86 are adjusted so that dV equals zero voltage thereby providing two balanced bridges and calibrating the measuring apparatus 104. The bridge is balanced individually with respect to the frequency of the exciting currents from the first current generating means 50 and the second current generating means 76.

The implementation of the invention as described above will be described below with reference to FIGS. 5 to 9 including several alternative embodiments, which additionally may be implemented in numerous ways. The invention may be implemented in accordance with a first embodiment comprise a bridge circuitry designated in its entirety by numeral 106 and shown as a circuit diagram in FIG. 5 having a power transmitter amplifier TA1 being supplied with an AC input signal at frequency F1.

The power transmitter amplifier TA1 provides a current excitation output, which is split into two equal excitation currents I1 in to two lines. The first line is connected to the coated first section 18 of the metal element 10 via a resistor R1A. The second line is connected to the non-coated second section 20 of the metal element 10 via a resistor R1B. The resistors R1A and R1B provide similar electrical resistance, which resistance is substantially larger than the electrical resistance of the coated first section 18 of the metal element 10 and the resistance of the non-coated second section 20 of the metal element 10. Since the resistors R1A and R1B are much larger than the resistance of the coated first section 18 and the non-coated second section 20 of the metal element 10, then the excitation current I1 will be substantially evenly distributed through resistors R1A and R1B even if the resistance of the coated first section 18 and the non-coated second section 20 of the metal element 10 is changing. The excitation current I1 induces a voltage $V_R$ across the reference or coated first section 18 of the metal element 10 and a voltage $V_C$ across the coupon or non-coated second section 20 of the metal element 10.

A subtraction of the voltages $V_C$ and $V_R$ constitute a voltage difference dV defined by the difference between $V_C$ and $V_R$. A differential sensor amplifier SA1 is connected across the entire length of the metal element 10 and measures and amplifies the differential voltage dV. Alternatively the sensor amplifier SA1 may amplify the voltages $V_C$ and $V_R$ individually by short circuiting the first section 18 or the second section 20 of the metal element respectively. The differential sensor amplifier SA1 provides an alternating output signal to a detector DF1 in turn providing a DC voltage to an output O1, which DC voltage may be measured by a sensitive voltmeter scaled in $\mu\Omega$ to indicate a differential resistance between the non-coated second section 20 and the coated first section 18 of the metal element 10 defined by $dR=R_C-R_R$.

Figure 5:
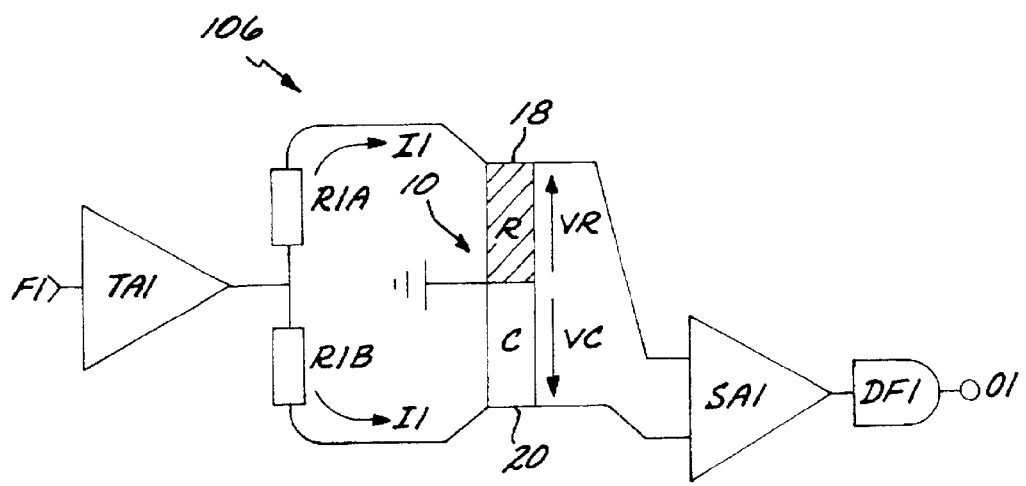
FIG. 5 shows a schematic circuit diagram of a first embodiment of the present invention constituted by a circuit for making an uncompensated measurement of the differential resistance.

The basic non-compensated bridge circuitry 106 shown in FIG. 5 may be improved by introducing temperature compensating means in order to prevent erroneous measurements caused by temperature effects. Therefore the first embodiment of the invention may further comprise temperature compensating circuitry as shown in FIG. 6 as a second embodiment of the present invention.

Figure 6:
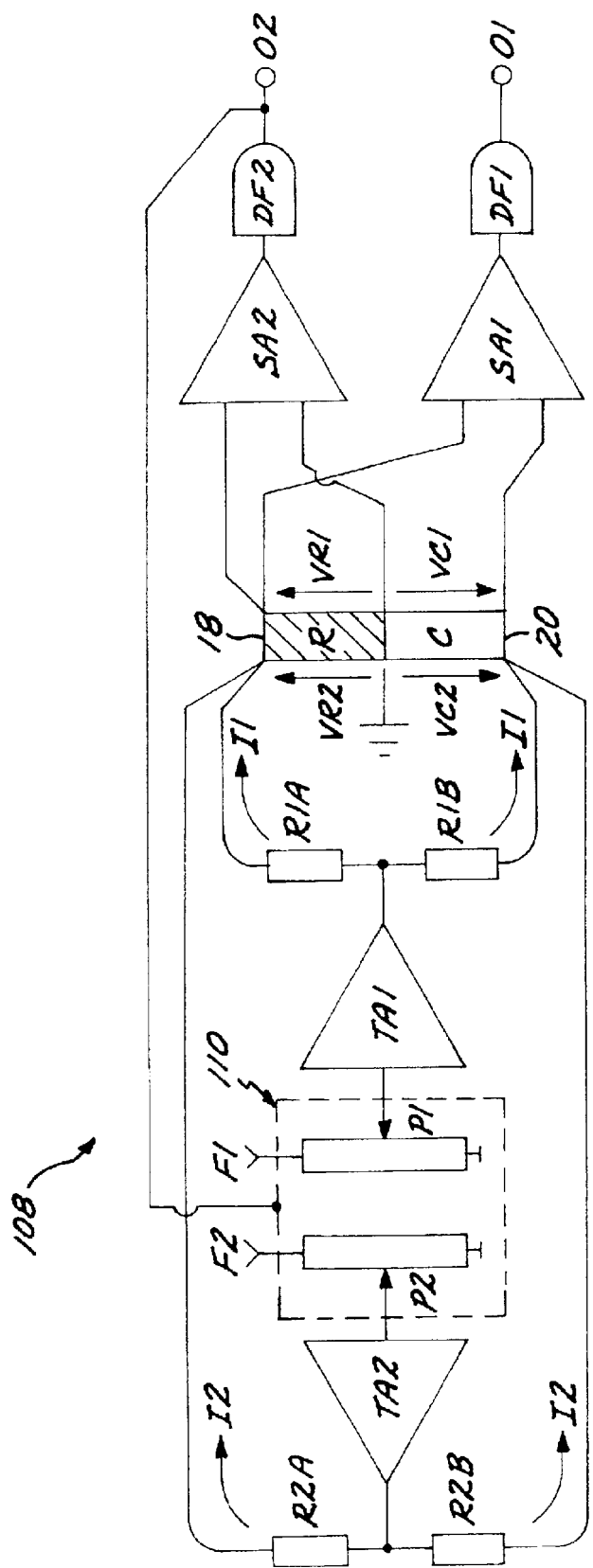
FIG. 6 shows a schematic circuit diagram of a second embodiment of the present invention constituted by a circuit for performing temperature compensated measurements of accumulated and instant rate of material loss or material gain.

FIG. 6 shows a circuit diagram of a temperature compensated bridge circuitry designated in its entirety by numeral 108. The circuitry 108 comprises a bridge circuit indexed by numeral 1, which bridge circuit to some extend is identical to the circuitry 106 shown in FIG. 5, and further comprises a temperature compensating circuit indexed by numeral 2. The temperature compensating circuit 110 comprises an input circuit designated by numeral 110 in its entirety for controlling the input excitation signals for the temperature compensated bridge circuitry 108. The input circuit is shown in FIG. 6 comprising two potentiometers P1 and P2. Alternative implementations of the input circuit 110 will be further described in detail with reference to FIG. 7.

As in the circuitry 106 shown in FIG. 5 the circuitry 108 comprises a first power transmitter amplifier TA1 being supplied with a first alternating input signal at a first frequency F1. The first frequency may be in the range 1 Hz to 100 KHz, such as ranges 50 Hz to 50 KHz, 500 Hz to 5 KHz or 1 KHz to 4 KHz, however, preferably the first frequency F1 of the first alternating input signal is 1.5 KHz.

The first power transmitter amplifier TA1 provides a first current excitation output at the first frequency F1, which current excitation output is split into two equal excitation currents I1 in to two lines. The first line is connected to the coated first section 18 of the metal element 10 via a resistor R1A. The second line is connected to the non-coated second section 20 of the metal element 10 via a resistor R1B. Since similarly as described with reference to FIG. 5 the resistors R1A and R1B are much larger than the resistance of the coated first section 18 and the non-coated second section 20 of the metal element 10 the excitation current I1 will be substantially evenly distributed through resistors R1A and R1B even if the resistance of the coated first section 18 and the non-coated second section 20 of the metal element 10 is changing. The excitation current I1 induces a voltage $V_{R1}$ across the coated first section 18 of the metal element 10 and a voltage $V_{C1}$ across non-coated second section 20 of the metal element 10.

A subtraction of the voltages $V_{C1}$, and $V_{R1}$ provides a first voltage difference $dV_1$ defined by the difference between $V_{C1}$ and $V_{R1}$. A first differential sensor amplifier SA1 is connected across the entire length of the metal element 10 and measures and amplifies the first differential voltage $dV_1$. Alternatively the sensor amplifier SA1 may amplify the voltages $V_C$ and $V_R$ individually by short circuiting the first section 18 or the second section 20 of the metal element respectively. The first differential sensor amplifier SA1 provides a first alternating output signal to a synchronous detector DF1 providing a first DC voltage to the output O1, which first DC voltage may be measured by a first sensitive voltmeter scaled in $\mu\Omega$ to indicate a differential resistance between the non-coated second section 20 and the coated first section 18 of the metal element 10 defined by $dR=R_C-R_R$. The first DC voltage may be in the range form −24V to +24V such as ranges −12V to +12V or −5V to +5V. However preferably the first DC voltage is in the range −1V to +1V.

The second embodiment of the invention in accordance with FIG. 6 further comprises a second power transmitter amplifier TA2 being supplied with a second alternating input signal at a second frequency F2.

The second power transmitter amplifier TA2 provides a second current excitation output having the second frequency F2, which current excitation output is split into two equal excitation currents I2 in to two lines. The second excitation current I2 is fed to the coated first section 18 and the non-coated second section 20 of the metal element 10 via resistors R2A and R2B, which resistors R2A and R2B are of the same order of magnitude as resistors R1A and R1B.

The first and the second input signals are fed to the first and second power transmitter amplifier TA1 and TA2 respectively through a input circuit 110 constituted by two the potentiometers P1 and P2. The potentiometers P1 and P2 provide two alternating voltage input signals to the first and second power transmitter amplifier TA1 and TA2 which input signals are substantially equal in voltage amplitude. The amplitude of the two alternating voltage input signals is controlled by the input circuit 110 on the basis of a feedback signal from a second DC voltage signal provided at a second output O2.

The excitation current I2 from the power transmitter amplifier TA2 induces voltages $V_{R2}$ and $V_{C2}$ at the second frequency F2 across the coated first section 18 and non-coated second section 20 of the metal element 10 simultaneously to the excitation current I1 induces the voltages $V_{R1}$ and $V_{C1}$ at the first frequency F1.

The first and second sensor amplifiers SA1 and SA2 provide the possibility for selective differential voltage measurements. And the first and second sensor amplifiers SA1 and SA2 through the synchronous detectors DF1 and DF2 respectively outputs a first DC voltage to a first output O1 and as well as the second DC voltage to the second output O2. The first DC voltage at the first output O1 is proportional to $V_{C1}-V_{R1}$ and the second DC voltage at the second output O2 is proportional to $V_{R2}$.

The second frequency F2 may be in the 1 Hz to 100 KHz, such as ranges 50 Hz to 50 KHz, 500 Hz to 5 KHz or 1 KHz to 4 KHz, however, preferably the second frequency F2 of the second AC input signal is 2.5 KHz. The second frequency F2 preferably is different from the first frequency F1 so as to ensure that the first and second selective sensor amplifier SA1 and SA2 may perform a frequency selective amplification of the voltages $V_{R2}$ and $dV_1$.

As mentioned above the second sensor amplifier SA2 controls the input circuit 110 constituted by the potentiometers P1 and P2 for the adjustment of the first and second alternating input voltage signals. If the resistance of the coated first section 18 of the metal element 10 should increase, caused by a higher temperature, then the second sensor amplifier SA2 and the second synchronous detector DF2 adjusts the two potentiometers in order to decrease the excitation currents I1 and I2 to keep $V_{R1}$, $V_{R2}$, $V_{C1}$ and $V_{C2}$ constant. In contrary if the resistance of the coated first section 18 of the metal element 10 should decrease, caused by a lower temperature, then the second sensor amplifier SA2 and the second synchronous detector DF2 adjusts the two potentiometers in order to increase the excitation currents I1 and I2 to keep $V_{R1}$, $V_{R2}$, $V_{C1}$ and $V_{C2}$ constant. The circuitry 108 ensures that the measured resistance of the non-coated second section 20 of the metal element 10 is unaffected by changes in temperature.

Figure 7:
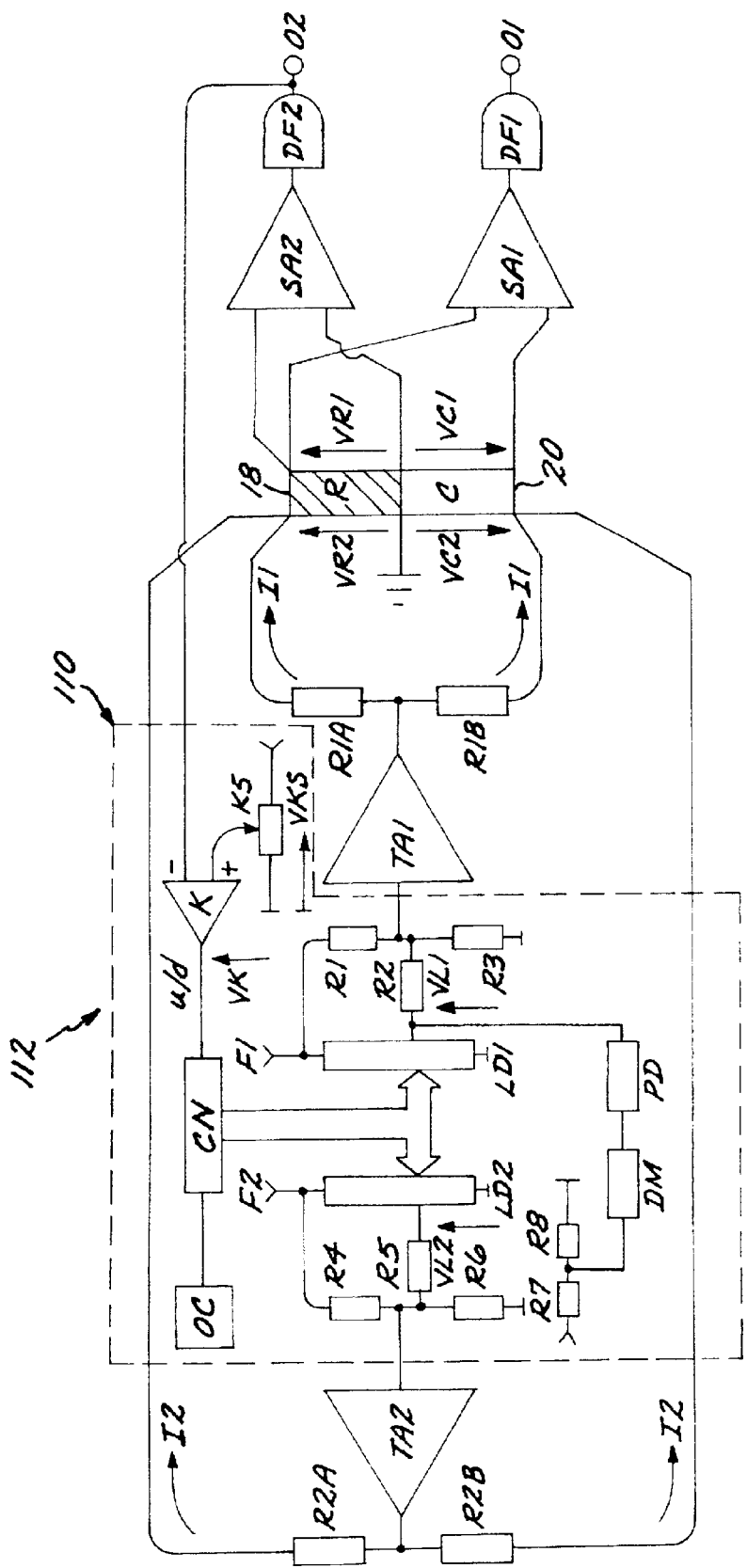
FIG. 7 shows a schematic circuit diagram of temperature compensating means included in the second embodiment of the present invention.

FIG. 7 shows a schematic circuit diagram of a temperature compensated circuit designated in its entirety by numeral 112 and including temperature compensating means included in the second embodiment of the present invention. The input circuit 110 shown in FIG. 7 is constituted by a first digital ladder LD1 and a second digital ladder LD2 both in parallel and governed by a digital binary up/down counter CN. The two digital ladders LD1 and LD2 perform digital to analogue conversion.

The input of the counter CN is clocked by an oscillator OC thus providing a rate of counting. The clock frequency may be in the range 5 Hz to 500 Hz such as ranges 20 Hz to 200 Hz preferably the clock frequency is 100 Hz. A comparator K performs a comparison of the second DC voltage signal at the second output O2 fed by the second synchronous detector DF2 and a reference DC voltage signal VKS provided by a reference potentiometer KS. On the basis of the comparison performed by the comparator K, the comparator K feeds an up or down count signal to the counter. The output state of the comparator K determines the direction of the count. A "high" for counting up, a "low" for counting down. "Low" and "high" in this context is a generic term for the logical "1" and logical "0" and the voltages defining "high" and "low" are limited in sized the maximum and minimum supply voltages used in the apparatus. The counter CN may be constituted by a counter in the range from 1 bit to 128 bits counter but preferably the counter CN is a 16 bit counter i.e. with a maximum of 4096 counts.

The first and second alternating input signals having frequencies F1 and F2 respectively is supplied to the two digital ladders LD1 and LD2, and the two digital ladders LD1 and LD2 provide a first ladder output VL1 having frequency F1 and a second ladder output VL2 having frequency F2. The first and second ladder outputs VL1 and VL2 have amplitudes proportional to the counter position. The amplitudes of the first and second ladder outputs VL1 and VL2 are at maximum at counter position 4096 and zero at counter position 0.

The first input signal to the power transmitter amplifier TA1 having frequency F1 is attenuated by resistor R1 and resistor R3 but superimposed by a certain amount of ladder output VL1 attenuated by resistor R2 and R3.

The second input signal to the power transmitter amplifier TA2 having frequency F2 is attenuated by resistor R4 and resistor R6 but superimposed with exactly the same amount via resistors R5 and R6 as in the first digital ladder LD1.

The number of counts in the counter CN provides the first and second excitation currents I1 and I2 and induces specific voltages $V_{C1}$, $V_{R1}$, $V_{C2}$ and $V_{R2}$ which in turn translates into the first DC voltage at the first output O1 induced by the first alternating input signal having frequency F1 and the second DC voltage at the second output O2 induced by the second alternating input signal having frequency F2. The first DC voltage is based on and converted from a selective voltage measurement and amplification of the differential voltage $dV_1$ embraced by the total differential voltage across the length of the metal element 10 induced by both of the excitation currents I1 and I2. The selective voltage measurement and amplification of the differential voltage $dV_1$ across the length of the metal element 10 is performed by the first sensor amplifier SA1 selecting frequency F1 and the conversion from AC to DC is performed by the first synchronous detector DF1. Similarly, the second DC voltage is based on and converted from a selective voltage measurement and amplification of the voltage $V_{R2}$ embraced by the total voltage across the coated first section 18 of the metal element 10 induced by both of the excitation currents I1 and I2. The selective measurement and amplification of the voltage $V_{R2}$ across the coated first section 18 of the metal element 10 is performed by the second sensor amplifier SA2 selecting frequency F2 and the conversion from AC to DC is performed by the second synchronous detector DF2.

The second DC voltage signal at the second output O2 is fed to an inverting input of the comparator K. A non-inverting input of the comparator K is provided with a reference DC voltage signal VKS provided by a reference potentiometer KS. The reference DC voltage signal VKS and the second DC voltage signal are within a range from −24V to +24V such as ranges −12V to +12V and −5V to +5V, however preferably the reference DC voltage signal VKS and the second DC voltage signal are in a range from 0V to +5V.

In case the temperature of the hostile environment or the environment in which the metal element 10 is located increases then the resistances of coated first section 18 and the non-coated second section 20 of the metal element 10 will increase and consequently the voltages $V_{C1}$, $V_{R1}$, $V_{C2}$ and $V_{R2}$ will increase causing an increase in the second DC voltage signal at the second output O2.

As the second DC voltage signal at the second output O2 increases to a higher value than the reference DC voltage signal VKS, the comparator K will provides a changing output signal VK e.g. changing from "high" to "low", causing the counter CN to count down. As the count is reduced the first and second digital ladder LD1 and LD2 will compensate for the temperature increase by ensuring that the first and second excitation currents I1 and I2 are reduced so as to provide a reduction of all voltages $V_{C1}$, $V_{R1}$, $V_{C2}$ and $V_{R2}$. A reduction of the voltage $V_{R2}$ will subsequently lead to a reduction of the second DC voltage signal. Since the reference DC voltage signal VKS is constant then the difference between the second DC voltage signal and the reference DC voltage signal VKS is reduced. The comparator K will in case the voltage difference between the second DC voltage and the reference voltage VKS still has the same polarity initiate a reduction of the counts in the counter CN and hence reduce the excitation currents I1 and I2 further. In case the polarity of the voltage difference between the second DC voltage and the reference voltage VKS changes then the comparator K will initiate an increase of the counts in the counter CN and hence increase the excitation currents I1 and I2.

Even during stable temperature conditions the counter CN in the temperature compensating circuit counts one or two counts up and down around a balance count e.g. 2000 so as to ensure that voltage difference between the second DC voltage at the second output O2 and the reference voltage VKS remains as small as possible.

Adjusting the reference voltage signal VKS by turning the potentiometer KS the counter CN may shift the balance count level to a lower balance count value (e.g. 1500) or greater balance count value (e.g. 2500).

The attenuation of the first ladder output VL1 is determined by a selection of resistors R2/R3 an the attenuation of the second ladder output VL2 is determined by a selection of resistors R5/R6 and these selections determine the influence of the temperature compensating circuit. The resistors R2, R3, R5 and R6 may be chosen so as to define a dynamic range, i.e. count from 0 to 4096, corresponding to a specific temperature interval (e.g. from 0 to 40° C.).

The implementation of the potentiometer KS providing the reference voltage VKS to the coder K has several benefits, which will be evident from the description presented below.

Since the metal element 10 may be configured in a wide variety of ways and constructed from a wide variety of materials the total resistance of the metal element 10 will change in accordance with material properties and dimension of the metal element 10. Hence the apparatus for measuring accumulated and instant rate of material loss or material gain should be capable of adapting to the wide variety of different metal elements. The implementation of the potentiometer KS allows the second embodiment of the present invention to be configured to any type of metal elements.

The resistance of a metal element 10 may be in the range 4 KΩ to 4 $\mu\Omega$ such as ranges to 4 mΩ to 400 mΩ or 10 mΩ to 100 mΩ. However, the second embodiment of the present invention may be implemented for any metal elements having any resistance. Depending on various design specifications for metal element 10 such as lifetime and sensitivity the coated first section 18 of the metal element 10 may have 10 mΩ resistance of the coated first section other applications apply a 100 mΩ resistance of the coated first section. Since the resistance of the coated first section determines $V_{R2}$, which subsequently determines the second DC output voltage at the second output O2, which in turn is compared with the reference voltage VKS it is imperative that the reference voltage VKS is adjustable so as to define an applicable temperature range.

The second embodiment of the present invention further comprises a discriminating circuit including a peak detector PD detecting peaks or alternatively detecting zeroes, positive going slopes or negative going slopes of either the first or the second ladder output signal VL1 and VL2 and providing a peak detector output DC voltage VL1DC, resistors R7 and R8 constituting a voltage divider and providing a fixed DC voltage, and a DC voltmeter DM connected to the peak detector PD and to the resistors R7 and R8 and providing a display of voltage differences between the peak detector output DC voltage VL1DC and the fixed DC voltage VDM. The peak detector PD and the resistors R7 and R8 are defined as a discriminator DIC and the DC voltmeter DM is defined as discriminator meter DM.

The discriminator meter DM indicates whether the voltage difference between the peak detector output DC voltage VL1DC and the fixed DC voltage is zero, positive or negative.

The peak detector PD is shown in FIG. 7 and is as an example connected to the first digital ladder LD1 output. The discriminating circuit will be described below in accordance with the connection presented in FIG. 7.

In case the counter CN has a maximum count at 4096. The desired balance voltage is achieved at count 2048, which count will provide a first ladder output VL1 and VL2 with half of maximum voltage amplitude. Further the peak detector output DC voltage VL1DC and the fixed DC voltage are identical when the count is 2048.

The discriminating circuit is utilized during initialization of the temperature compensated circuit 112 using one specific type of metal element 10. When starting a measurement with a specific type of metal element 10, the procedure is adjust the potentiometer KS until a mid-scale indication on the discriminator meter DM is achieved. If the temperature compensating circuit including the discriminator DIC is designed for a dynamic temperature range of 40° C., and the discriminator meter DM is scaled plus and minus 20° C., then the discriminator meter DM indicates the change in temperature.

Figure 8:
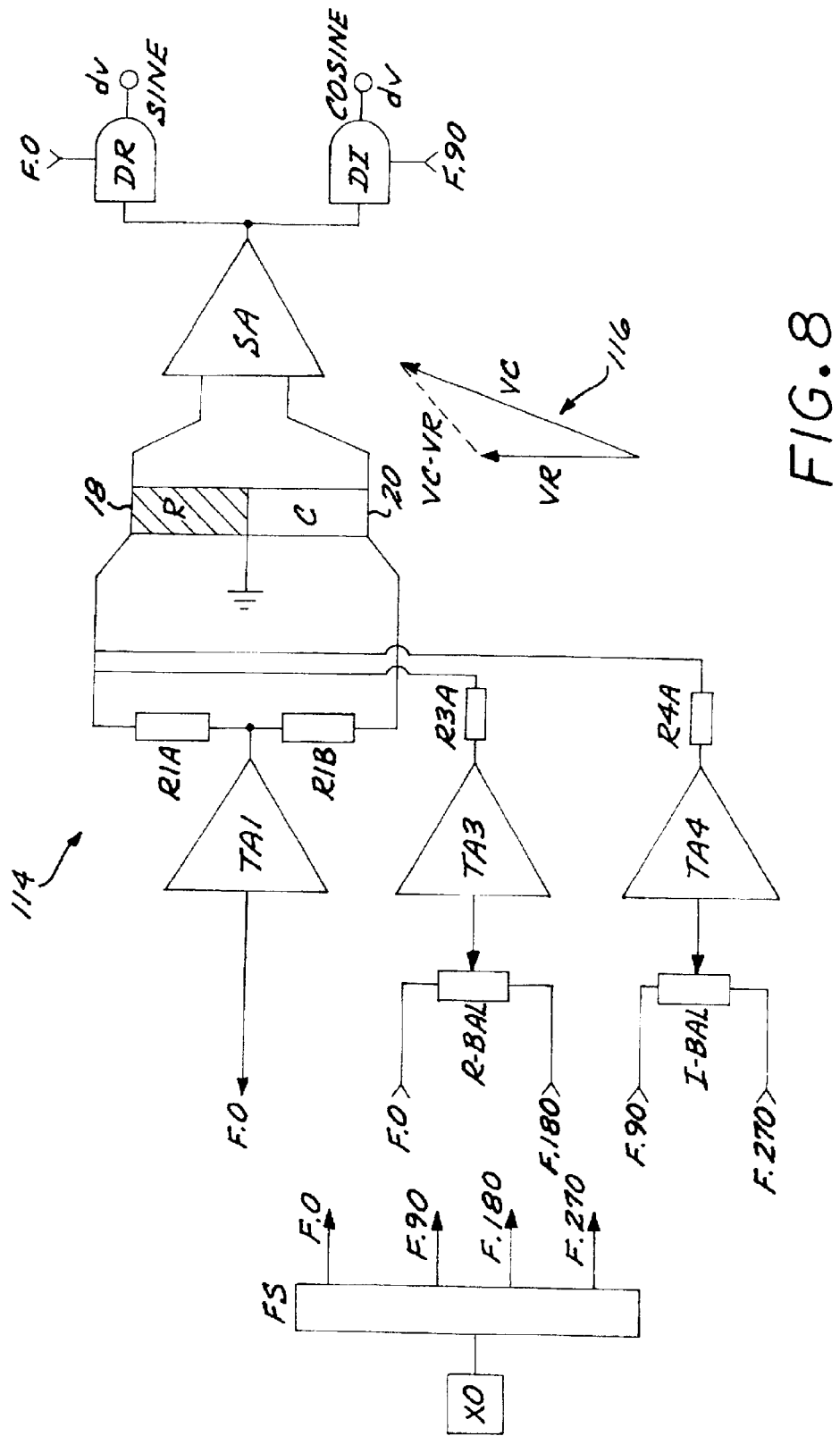
FIG. 8 shows a schematic circuit diagram of a balancing circuit for balancing of a bridging circuit during initialization.

Since the material loss or material gain of the second section 20 of the metal element 10 may constitute a change in impedance rather than simply a change in resistivity the invention in accordance with the second embodiment of the present invention further may include means for determining the impedance of the second section of the metal element 10. FIG. 8 shows a schematic circuit diagram of an impedance sensitive circuit designated in its entirety by numeral 114. As the second section 20 of the metal element is placed in a measurement environment the material gain or loss may provide changes in the material properties, which changes are best described as changes in complex impedance. Voltages $V_C$, $V_R$ and the difference dV equal to $V_C - V_R$ are therefore illustrated as vectors 116 and shown in FIG. 8. It is desirable to measure both a real and a imaginary vector component of the impedance $Z_R$ of the coated first section 18, the impedance $Z_C$ of the non-coated second section 20 and the impedance difference dZ between the first and second section 18, 20 of the metal element 10 namely $dZ = Z_C - Z_R$.

The real or sine part of an impedance is a generic term for a vector component of the impedance which is in phase with the excitation signal and the imaginary of cosine part of the impedance is a generic term for the vector component of the impedance in quadrature to the excitation current.

The impedance sensitive circuit 114 comprises three power transmitter amplifiers TA1, TA3 and TA4 introducing no phase delay between the input of the transmitter amplifiers TA1, TA3 and TA4 and the output of the transmitter amplifiers TA1, TA3 and TA4. Thus the excitation currents from the three transmitter amplifiers TA1, TA3 and TA4 are always in phase with the signal applied to the inputs of the transmitter amplifiers TA1, TA3 and TA4.

The first power transmitter amplifier TA1 provides a excitation current to a bridge circuit incorporating the essential features of the bridge circuit described with reference to FIG. 6. Additionally the second embodiment of the present invention incorporates the temperature compensating means described with reference to FIG. 7.

During initialization the bridge circuit is balanced by compensating for differences in voltages $V_C$ and $V_R$ so as to obtain an initial zero indication of dZ or alternatively as close to zero as possible. The impedance sensitive circuit 114 further comprises two balancing circuits for balancing the bridge circuit during initialization and a real and imaginary output circuit.

The balancing circuits provide balancing of the bridge circuit for both the real and the imaginary part of the vector dZ. The third power transmitter TA3 provides balancing of the real component of the vector dZ and the fourth power transmitter amplifier TA4 provides balancing of the imaginary component of the vector dZ.

A crystal designated by XO in FIG. 8 provides a square-wave signal to a four-quadrant phase splitter FS. The four-quadrant phase splitter FS provides square-wave signals having frequency F in 4 phases 0°, 90°, 180° and 270°, i.e. shifted by a 90°-phase delay from each other.

The first square-wave signal having frequency F and phase 0° designated by F.0 is fed to the power transmitter amplifier TA1, which in turn provides the first excitation current, through resistors R1A and R1B to the coated first section 18 and the non-coated second section 20 of the metal element 10.

Additionally the first square-wave signal F.0 in conjunction with the third square-wave signal having frequency F and phase 180° designated by F.180 is fed to real balance potentiometer R-BAL. The real balance potentiometer R-BAL provides a real balance potentiometer output signal fed to the input of the third power transmitter amplifier TA3, which in turn provides a third excitation current through resistor R3A to the coated first section 18 of the metal element 10.

The second square-wave signal having frequency F and phase 90° designated by F.90 and the fourth square-wave signal having frequency F and phase 270° designated by F.270 are fed to imaginary balance potentiometer I-BAL (imaginary in this context is to be construed as in vector terminology). The imaginary balance potentiometer I-BAL provides an imaginary balance potentiometer output signal fed to the fourth power transmitter amplifier TA4, which in turn provides a fourth excitation current through resistor R4A to the coated first section 18 of the metal element.

Depending on the position of R-BAL potentiometer the third power transmitter amplifier TA3 provides the third excitation current having phase 0° or phase 180°.

The third excitation current is added to or subtracted from the first excitation current provided by the first power transmitter amplifier TA1 and a second excitation current provided by the second power transmitter amplifier TA2.

Depending on the position of the I-BAL potentiometer the fourth power transmitter amplifier TA4 provides the fourth excitation current having phase 90° or phase 270°. The fourth excitation current is added in quadrature to the first and second excitation currents provided by the first and second power transmitter amplifier TA1 and TA2 in the direction 90° or 270°.

The balancing circuits enable that the complex voltage $V_R$ across coated first section 18 of the metal element 10 may be adjusted so that the voltage difference $dV=V_C-V_R$ is reduced to zero or at least reduced to an acceptable small voltage. The acceptable voltage may be determined in accordance with a factor of the expected voltage variations induced by material gain or loss.

The differential voltage $dV=V_C-V_R$ is fed to a sensor amplifier SA, which provides an output signal to two synchronous detectors DR and DI. The synchronous detector DR is synchronized by phase 0° and consequently outputs a DC voltage proportional to the sine value of dV. The synchronous detector DI is synchronized by phase 90° and consequently outputs a DC voltage proportional to the cosine value of dV.

Figure 9:
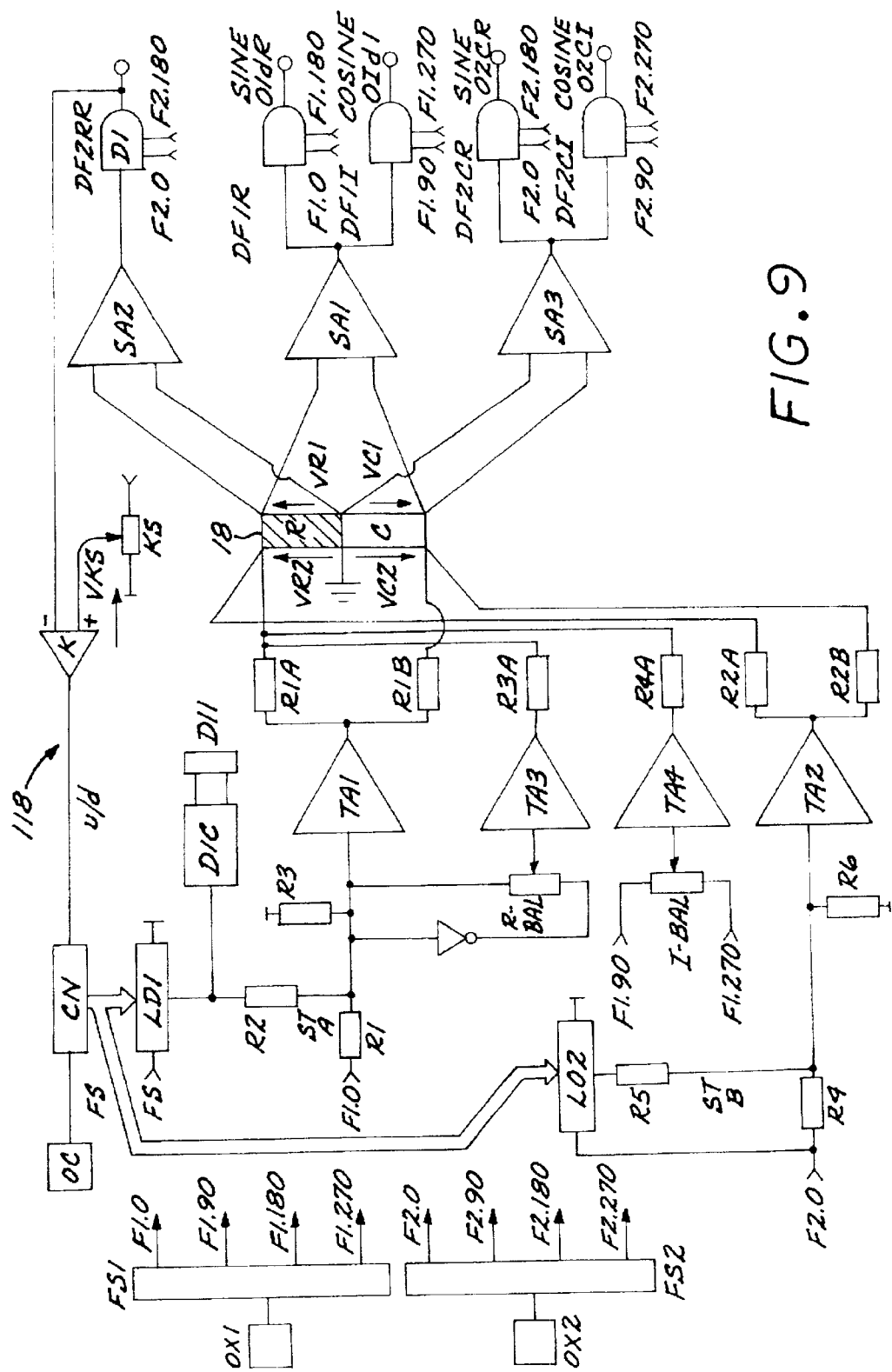
FIG. 9 shows a schematic circuit diagram of the third embodiment of the invention constituted by a complete circuit including balancing circuit, temperature compensation circuit and impedance measurement circuit for determining accumulated and instant rate of material loss or material gain.

FIG. 9 shows a circuit diagram of a complete circuit 118 constituting a third embodiment of the invention. The complete circuit 118 comprises all the features described with reference to FIGS. 1 through 8.

A first crystal designated by XO1 in FIG. 9 provides a first square-wave signal to a first four-quadrant phase splitter FS1. The first four-quadrant phase splitter FS1 provides square-wave signals in 4 phases at 0°, 90°, 180° and 270° at a first frequency F1, i.e. shifted by a 90°-phase delay from each other.

Similarly a second crystal designated by XO2 provides a second square-wave signal to a second phase splitter FS2 providing 4 phase-signals at a second frequency F2, 0°, 90°, 180° and 270° phases. These signals are used as phase reference inputs for five synchronous detectors DF1R, DF1I, DF2CR, DF2CI and DF2RR and as signal inputs for balance potentiometers I-BAL and R-BAL, power transmitter amplifiers TA1, TA2, TA3 and TA4 and first and second digital ladders LD1 and LD2.

A third crystal OC provides a clock pulse to a counter CN and a comparator K supplies up/down commands to the counter CN. The counter CN provides a digital binary count output signal to digital binary inputs of the first and second digital ladder LD1 and LD2.

The first square-wave signal having phase 0° and frequency F1 is fed to a frequency input of the first digital ladder LD1 and to the first power transmitter amplifier TA1 via resistor R1. The first power transmitter amplifier TA1 further receives input from the first digital ladder LD1 via resistor R2, both signals attenuated by resistor R3.

The power transmitter amplifier TA1 supplies a first excitation current having the frequency F1 to the first section 18 and the second section 20 of the metal element 10 via resistors R1A and R1B.

Additionally the first square-wave signal having phase 0° and frequency F1 is fed to a first input point of a balancing potentiometer R-BAL and to an inverter I. The inverter I provides an inversion of the first square-wave signal to the second input point of the balancing potentiometer R-BAL. The balancing potentiometer R-BAL feeds an input signal to the third power transmitter amplifier TA3, which in turn provides a third excitation current via a resistor R3A to the coated first section 18 of the metal element 10. The third excitation current enables balancing of the real component of the impedance difference between the coated first section 18 and the non-coated second section 20.

The first square-wave signal having frequency F1 and phases 90° and 270° is feed to a second balancing potentiometer I-BAL, which in turn provides a fourth power transmitter amplifier TA4. The fourth power transmitter amplifier TA4 supplies a fourth excitation current enabling balancing of the cosine or imaginary component of the impedance difference between the coated first section 18 and the non-coated second section 20 via resistor R4A.

The second square-wave signal having frequency F2 and phase 0° is fed to a frequency input of the second digital ladder LD2 and to the second power transmitter amplifier TA2 via resistor R4. The second power transmitter amplifier TA2 further receives input from the second digital ladder LD2 via resistor R5, both signals are attenuated by resistor R6.

The second power transmitter amplifier TA2 supplies a second excitation current having the frequency F2 to the first section 18 and the second section 20 of the metal element 10 via resistors R2A and R2B.

All four excitation currents induce voltages $V_{R1}$ and $V_{C1}$ at frequency F1 and voltages $V_{R2}$ and $V_{C2}$ at frequency F2 across the coated first section 18 and the non-coated second section 20 of the metal element 10.

A subtraction of voltages $V_{C1}$ and $V_{R1}$ induced across the non-coated second section 20 and the coated first section 18 by the first excitation current provide a difference voltage dV1, which is amplified by a sensor amplifier SA1 and subsequently fed to first real and imaginary detectors DF1R and DF1I respectively.

The first real detector DF1R utilizes the first square-wave signal having the frequency F1 and phases 0° and 180° for the provision of a first DC voltage signal proportional to the vector component of $V_{C1}$ minus $V_{R1}$ in phase with the first square-wave signal having frequency F1 and phase 0° (i.e. the sine output) on a first output O1dR.

The first imaginary detector DF1I utilizes the first square-wave signal having the frequency F1 and phases 90° and 270° for the provision of a second DC voltage signal proportional to the vector component of $V_{C1}$ minus $V_{R1}$ in quadrature phase with the first square-wave signal having frequency F1 and 0° (i.e. the cosine output) on a second output O1dI.

A voltage $V_{C2}$ induced across the non-coated second section 20 of the metal element 10 by the second excitation current is amplified by a third sensor amplifier SA3 and subsequently fed to a second real and imaginary detector DF2CR and DF2CI respectively.

The second real detector DF2CR utilizes the second square-wave signal having the frequency F2 and phases 0° and 180° for the provision of a third DC voltage signal proportional to the vector component of $V_{C2}$ in phase with the second square-wave signal having frequency F2 and phase 0° (i.e. the sine output) on a third output O2CR.

The second imaginary detector DF2CI utilizes the second square-wave signal having the frequency F2 and phases 90° and 270° for the provision of a fourth DC voltage signal proportional to the vector component of $V_{C2}$ in quadrature phase with the second square-wave signal having frequency F2 and 0° (i.e. the cosine output) on a fourth output O2CI.

A voltage $V_{R2}$ induced across the coated first section 18 of the metal element 10 by the second excitation current is amplified by a second sensor amplifier SA2 and subsequently fed to a third detector DF2RR. The third detector DF2RR utilizes the second square-wave signal having the frequency F2 and phases 0° and 180° for the provision of a fifth DC voltage signal proportional to the $V_{R2}$ on a fifth output O2RR (the voltage $V_{R2}$ has no quadrature component).

The fifth DC voltage provided at the fifth output O2RR is fed to an inverting input of the comparator K. A non-inverting input of the comparator K is connected to a reference potentiometer KS providing a reference DC voltage to the non-inverting input. The comparator K provides up/down signals to the counter CN in order to control the direction of count. A discriminator DIC and an associated discriminator meter DM as described with reference to FIG. 7 is connected to the output of the first digital ladder LD1 and determine the correct adjustment of the reference potentiometer KS.

The third embodiment of the invention as shown in FIG. 9 as the complete circuit 118 may include switching means for connecting or disconnecting the temperature compensating means. A switch STA/STB provides this feature by disconnecting the first and second digital ladder LD1 and LD2 from the complete circuit 118.

The temperature compensating circuit 110, the impedance sensitive circuit 114 or in fact the complete circuit 118, shown in FIG. 6 through 9, may be implemented utilizing several physically separated electronic elements or be implemented as a single electronic element such as an application specific integrated circuit. The operations to be performed by the apparatus may further be implemented in any configuration of hardware and in any configuration of software. In particular logical and arithmetic operations may be performed utilizing a control unit as a further alternative embodiment of the present invention.

A control unit such as a central processing unit (CPU), microprocessors, microprocessors integrating random access memory (RAM) or read only memory (ROM), and/or a microcontroller is incorporated for performing temperature compensating operations and for calculating values for corrosion parameters e.g. reduction of thickness a, temperature correcting factor and corrosion rate. The control unit comprises internal or external storage means for storing measurement data and comprises means for facilitating transferring measurement data to a personal computer is implemented to perform Data representing the measured impedance of the metal element 10 such as the real- and imaginary vector component of the impedance $Z_R$ of the coated first section 18, the impedance $Z_C$ of the non-coated second section 20 and the impedance difference dZ between the first and second sections 18, 20 of the metal element 10, namely $dZ=Z_C-Z_R$ are converted into digital signals and input to the processor.

Further data input to the apparatus includes operator input, such as identification codes for each metal element utilized by the processor to identify a particular metal element as well as individual metal element characteristics including the initial thickness σ of the metal elements, temperature coefficients α of the material of the metal elements, and the initial resistance $R_0$ of the metal element at a specific temperature. Additionally, the operator input comprises time period (days, hours and minutes) Δt defining the duration of the measurement, and finally, number of measurements N to be performed during measurement of the metal gain or the metal loss.

The above-listed inputs are utilized by the processor in calculating temperature T of the coated first section 18 of the metal element, reduction or gain of metal element thickness Δσ, time increments dt of measurements of metal gain or metal loss rate, temperature correction factor $T_c$ and, finally, the instant rate of metal gain or metal loss, e.g. corrosion rate $V_{corr}$. Further, the processor provides an output of the real- and imaginary vector components of the coated first section and the non-coated second section of the metal element, and, finally, the real- and imaginary vector component of the impedance difference between the first and second sections of the metal element (differential impedance).

The processor may utilize the below algorithm for calculating the temperature T of the metal element, when the temperature coefficient a of the metal element is given in 0/00 per unit of temperature change:

$$T(° C.) = \frac{\ln \frac{R_{R,out}}{R_0}}{\ln(1 + \frac{\alpha}{1000})}$$

where the term $R_{R,out}$ is the real vector component of the impedance of the coated first section of the metal element.

The processor may further utilize the below or a familiar algorithm—as defined by the shape and geometric form of the metal element, in below algorithm a plate geometry—for calculating the degree of metal gain or metal loss (corrosion) of the metal element:

$$\Delta\sigma = \sigma \cdot \left(1 - \frac{R_{C,ini}}{R_{R,ini}} \cdot \frac{R_{R,out}}{R_{C,out}}\right)$$

The term $R_{c,ini}$ is to be construed as the initial real vector component of the impedance of the non-coated second section of the metal element, the term $R_{R,ini}$ is to be construed as the initial real vector component of the impedance of the coated first section of the metal element, the term $R_{R,out}$ at is to be construed as a measured real vector component of the coated first section of the metal element, and, finally, the term $R_{C,out}$ is to be construed as a measured value of the real vector component of the impedance of the non-coated second section of the metal element.

Further, the processor may utilize the below algorithm for determining the term increments dt:

$$dt = \frac{\Delta t}{N}$$

The processor may be implemented so as to reconfigure the dates, hours and minutes incorporated in Δt to e.g. minutes.

Further, the processor may utilize the below algorithm for determining the temperature correcting factor $T_c$:

$$T_c = \frac{R_0}{R_{R,out}}$$

Finally, the processor may utilize the below algorith for determining the metal gain or metal loss (corrosion) rate, $V_{corr,n+1}$ in the case of plate geometry for the metal element:

$$V_{corr,n+1} = \frac{T_{c,n+1} \cdot dR_{C,n+1} - T_{c,n} \cdot dR_{C,n}}{dt} \cdot \frac{R_{R,out,n+1} \cdot \sigma}{R_{C,out,n+1}^2} \cdot K$$

The term $V_{corr,n+1}$ is to be construed as the corrosion rate at the time corresponding to the n+1 measurement, the term $T_{C,n+1}$ is to be construed as the temperature correcting factor at the time corresponding to the n+1 measurement, the term $dR_{C,n+1}$ is to be construed as the real vector component of the impedance difference between the second and the first sections of the metal element (differential impedance) at the time corresponding to the n+1 measurement, the term $T_{C,n}$ is to be construed as the temperature correcting factor at the time corresponding to ht n measurement, the term $dR_{C,n}$ is to be construed as the real vector component of the impedance difference between the second and first sections of the metal element (differential impedance) at the time corresponding to the n measurement, the term $R_{R,out,n+1}$ is to be construed as the real vector componnent of the impedance of the coated first section of the metal element at the time corresponding to the n+1 measurement, the term $R_{C,out,n+1}$ is to be construed as the real vector component of the impedance of the non-coated second section of the metal element at the time corresponding ot the n+1 measurement, and, finally, K is to be construed as a constant for configuring the output corrosion rate into a particular dimension such as mm/year.

The first fraction of the multiplication describes the temperature corrected changes of the real vector component of the impedance differense between the non-coated second section and the coated first section of the metal element (differential impedance) during a time increment. By adjusting the values of $\Delta t$ and N the operator may control the algorithm and in particular by either reducing $\Delta t$ or increasing N increase dt so as to achieve higher accuracies in the measurement.

What is claimed is:

1. An apparatus for measuring accumulated and instant rate of material loss or material gain and comprising:

(a) a DC supply supplying said apparatus with power to perform measuring operations end said DC supply defining a positive DC voltage and a negative DC voltage;

(b) a metal element defining a coated section having a first connector, a non-coated section having a second connector, and an interface having a third connector, said interface providing electrical and thermal connection between said coated section and said non-coated section experiencing corrosion or metal deposition in a measurement environment;

(c) a first input power system generating a first system input signal and generating an interface input signal to said third connector of said metal clement;

(d) a first power transmitter amplifier having a first power transmitter input receiving said first system input signal and having a first power transmitter output generating a first excitation output signal;

(e) a first resistor for interconnecting said first power transmitter output and said first connector of said coated section of said metal element so as to constitute a first path of said first excitation output signal from said first power transmitter output through said first resistor and said coated section of said metal element to said third connector of said metal element, said first excitation output signal inducing a first metal element voltage across said coated section of aaid metal element;

(e) a second resistor for interconnecting said first power transmitter output and said second connector of said non-coated section of said metal element so as to constitute a second path of said first excitation output signal from said first power transmitter output through said second resistor and said non-coated section or said metal element to said third connector of said metal element, said first excitation output signal further inducing a second metal element voltage across said non-coated section of said metal element; and (f) a first sensor amplifier having a first sensor amplifier input connected to said first connector of said coated section of said metal element, having a second sensor amplifier input connected to said second connector of said non-coated section of said metal element, and having a first sensor output generating a first sensor amplifier output signal constituted by an amplification of said first metal element voltage, said second metal element voltage and/or a voltage difference between said second metal element voltage and said first metal element voltage;

said metal element defining a first resistance between said first connector of said coated section and said third connector of said metal element and a second resistance between said second connector of said non-coated section and said third connector of said metal element, wherein said second resistance increases as a function of corrosion and decreases as a function of metal deposition so as to induce said voltage difference between said second metal element voltage and said first metal element voltage.

2. The apparatus according to claim 1, wherein said metal element defines a predetermined cross sectional shape, wherein said metal element comprises a metallic composition, and wherein said interface of said metal element provides an electrical and a thermal connection between said coated section and said non-coated section, the interface being provided by a structure selected from the group consisting of at least one of an electrically and thermally conductive wire, a direct contact between said coated section and said non-coated section, and a boundary between said coated section and said non-coated Section constituted by a piece including a metal.

3. The apparatus according to either of claim 1 or 2, wherein said first system input signal is a voltage signal having a first frequency in the range of about 1 Hz to about 100 KHz; wherein said second system input signal is a voltage signal having a second frequency in the range of about 1 Hz to about 100 KHz; wherein said first power transmitter amplifier provides said first excitation output signal comprising a, square-wave current signal having said first frequency; wherein said second power transmitter amplifier provides said second excitation output signal comprising a square-wave current signal having said second frequency; wherein said first sensor amplifier provides a frequency selective amplification of part of said first metal element voltage and said second metal clement voltage constituted by said first frequency; and wherein said second sensor amplifier provides a selective amplification of part of said first metal element voltage constituted by said second frequency.

4. The apparatus according to claim 1, wherein said conversion of said first sensor amplifier output signal performed by said first detector is performed by converting said alternating first sensor amplifier output signal into a first DC voltage signal in the range of about −24V to about +24V; and wherein said conversion of said second sensor output signal performed by said second detector is performed by converting said alternating second sensor output signal into a second DC voltage signal in the range of about −24V to about +24V.

5. The apparatus according to claim 1, wherein said first and second resistances of said metal element are in a range from about 4 $\mu\Omega$ to about 4 K$\Omega$.

6. An apparatus for measuring accumulated and instant rate of material loss or material gain, comprising:

(a) a DC supply supplying said apparatus with power to perform measuring operations and said DC supply defining a positive DC voltage and a negative DC voltage;

(b) a metal element defining a coated section having a first connector, a non-coated section having a second connector, and an interface having a third connector, said interface providing electrical and thermal connection between said coated section and said non-coated section experiencing corrosion or metal deposition in a measurement environment;

(c) a first input power system generating a first system input signal and generating an interface input signal to said third connector of said metal element, (d) a first power transmitter amplifier having a first power transmitter input receiving said first system input signal and having a first power transmitter output generating a first excitation output signal;

(e) a first resistor for interconnecting said first power transmitter output arid said first connector of said coated section of said metal element so as to constitute a first path of said first excitation output signal from said first power transmitter output through said first resistor and said coated section of said metal element to said third connector of said metal element, said first excitation output signal inducing a first metal element voltage across said coated section of said metal element;

(f) a second resistor for interconnecting said first power transmitter output and said second connector of said non-coated section of said metal element so as to constitute a second path of said first excitation output signal from said first power transmitter output through said second resistor and said non-coated section of said metal element to said third connector of said metal element, said first excitation output signal further inducing a second metal element voltage across said non-coated section of said metal element;

(g) a first sensor amplifier having a first sensor amplifier input connected to said first connector of said coated section of said metal element, having a second sensor amplifier input connected to said second connector of said non-coated section of said metal element, and having a first sensor output generating a first sensor amplifier output signal constituted by an amplification of said first metal element voltage, said second metal element voltage and/or a voltage difference between said second metal element voltage and said first metal element voltage, said metal element defining a first resistance between said first connector of said coated section and said third connector of said metal element and a second resistance between said second connector of said non-coated section and said third connector of said metal element, said second resistance increasing as a function of corrosion and decreasing as a function of metal deposition so as to induce said voltage difference between said second metal element voltage and said first metal element voltage;

(h) a first detector having a first detector input receiving said first sensor amplifier output signal from said first sensor amplifier output, performing a conversion of said first sensor amplifier output signal and generating a first detector output signal;

(i) a second input power system generating a second system input signal arid generating said interface input signal to said third connector of said metal element;

(j) a second power transmitter amplifier having a second power transmitter input receiving a second system input signal and having a second power transmitter output generating a second excitation output;

(k) a third resistor for interconnecting said second power transmitter output and said first connector of said coated section of said metal element so as to constitute a first path of said second excitation output signal from said second power transmitter output through said third resistor and said coated section of said metal element to said third connector of said metal element, said second excitation output signal inducing, in cooperation with said first excitation output signal, said first metal element voltage across said coated section of said metal element;

(l) a fourth resistor for interconnecting said second power transmitter output and said second connector of said non-coated section of said metal element so as to constitute a second path of said second excitation output signal from said second power transmitter output through said fourth resistor and said non-coated section of said metal element to said third connector of said metal element, said second excitation output signal further inducing, in cooperation with said first excitation output signal, said second metal element voltage across said non-coated section of said metal element;

(m) a second sensor amplifier having a third sensor amplifier input connected to said first connector of said coated section of said metal element, having a fourth sensor amplifier input connected to said third connector of said metal element, and having a second sensor amplifier output generating a second sensor output signal constituted by an amplification of said first metal element voltage;

(n) a second detector having a second detector input receiving said second sensor output signal from said second sensor amplifier output, performing a conversion of said second sensor amplifier output, and generating a second detector output signal; and (o) a temperature compensating feedback circuit for compensating temperature induced variations in said first and second resistance of said metal element and utilizing said second detector output in controlling the amplitude of said first system input signal and said second system input signal so as to decrease said first system input signal and said second system input signal when said first resistance increases and so as to increase said first system input signal and said second system input signal when said first resistance decreases.

7. The apparatus according to claim 6, wherein said metal element defines a predetermined cross sectional shape; wherein said metal clement comprises a metallic composition and wherein said interface of said metal element providing an electrical and a thermal connection between said coated section and said non-coated section comprises a structure selected from the group consisting of at least one of an electrically and thermally conductive wire, a direct contact between said coated section and said non-coated section, and a boundary between said coated section and said non-coated section constituted by a piece including a metal.

8. The apparatus according to ether of claim 6 or 7, wherein said first system input signal is a voltage signal having a first frequency in the range of about 1 Hz to about 100 KHz; wherein said second system input signal is a voltage signal having a second frequency in the range of about 1 Hz to about 100 KHz wherein said first power transmitter amplifier provides said first excitation output signal comprising a square-wave current signal having said first frequency; wherein said second power transmitter amplifier provides said second excitation output signal comprising a square-wave current signal having said second frequency; wherein said first sensor amplifier provides a frequency selective amplification of part of said first metal element voltage and said second metal element voltage constituted by said first frequency; and wherein said second sensor amplifier provides a selective amplification of part of said first metal element voltage constituted by said second frequency.

9. The apparatus according to claim 6, further comprising:
(p) a first phase detective means connected to said first sensor amplifier output and performing a phase selective conversion of said first sensor amplifier output signal to a first real vector component voltage and a first imaginary vector component voltage of said voltage difference between said second metal element voltage and said first metal element voltage having said first frequency;
(q) a third sensor amplifier having a fifth sensor amplifier input connected to said second connector of said non-coated section of said metal element, having a sixth sensor amplifier input connected to said third connector of said metal element, and having a third sensor amplifier output generating a third sensor output signal constituted by an amplification of said part of said second metal element voltage having said second frequency;
(r) a second phase detective moans connected to said third sensor amplifier output and performing a phase selective conversion of said third sensor amplifier output signal to second real vector component voltage and a second imaginary vector component voltage of said second metal element voltage having said second frequency;
(s) a real vector component balancing circuit having a real vector component balancing circuit output generating a real balancing output signal and a real vector component balancing circuit input receiving said first system input signal;
(t) a third power transmitter amplifier having third power transmitter input connected to said real vector component balancing circuit output and having a third power transmitter output connected to said first connector on said coated section of said metal element and generating a third power transmitter output signal for balancing of said first real vector component voltage,
(u) an imaginary vector component balancing circuit having an imaginary vector component balancing circuit output generating an imaginary balancing output signal and an imaginary vector component balancing circuit input receiving said first system input signal phase shifted by 90° and 270°; and
(v) a fourth power transmitter amplifier having fourth power transmitter input connected to said imaginary vector component balancing circuit output and having a fourth power transmitter output connected to said first connector on said coated section of said metal element and generating a fourth power transmitter output signal for balancing of said first imaginary vector component voltage.

10. The apparatus according to claim 6, wherein said conversion of said first sensor amplifier output signal performed by said first detector is preformed by converting said alternating first sensor amplifier output signal into a first DC voltage signal in the range of about −24V to about +24V; and wherein said conversion of said second sensor output signal performed by said second detector is performed by converting said alternating second sensor output signal into a second DC voltage signal in the range of about −24V to about +24V.

11. The apparatus according to claim 6, wherein said first and second resistances of said metal element are in a range from about 4 $\mu\Omega$ to about 4 K$\Omega$.

12. An apparatus for measuring accumulated and instant rate of material loss or material gain and comprising:
(a) DC supply supplying said apparatus with power to perform measuring operations and said DC supply defining a positive DC voltage and a negative DC voltage;
(b) a metal element defining a costed section having a first connector, a non-coated section having a second connector, and an interface having a third connector, said interface providing electrical and thermal connection between said coated section and said non-coated section experiencing corrosion or metal deposition in a measurement environment;
(c) a first input power system generating a first system input signal and generating an interface input signal to said third connector of said metal element;
(d) a first power transmitter amplifier having a first power transmitter input receiving said first system input signal and having a first power transmitter output generating a first excitation output signal;
(e) a first resistor for interconnecting said first power transmitter output and said first connector of said coated section of said metal element so as to constitute a first path of said first excitation output signal from said first power transmitter output through said first resistor and said coated section of said metal element to said third connector of said metal element, said first excitation output signal inducing a first metal element voltage across said coated section of said metal element;
(f) a second resistor for interconnecting said first power transmitter output and said second connector of said non-coated section of said metal element so as to constitute a second path of said first excitation output signal from said first power transmitter output through said second resistor and said non-coated section of said metal element to said third connector of said metal element, said first excitation output signal further inducing a second metal element voltage across said non-coated section of said metal element;
(g) a first sensor amplifier having a first sensor amplifier input connected to said first connector of said coated section of said metal element, having a second sensor amplifier input connected to said second connector of said non-coated section of said metal element, and having a first sensor output generating a first sensor amplifier output signal constituted by an amplification of said first metal element voltage, said second metal element voltage and/or a voltage difference between said second metal element voltage and said first metal element voltage;

said metal element defining a first resistance between said first connector of said coated section and said third connector of said metal element and a second resistance between said second connector of said non-coated section and said third connector of said metal element, wherein said second resistance increases as a function of corrosion and decreases as a function of metal deposition so as to induce said voltage difference between said second metal element voltage and said first metal element voltage;

(h) a first detector having a first detector input receiving said first sensor amplifier output signal from said first sensor amplifier output, performing a conversion of said first sensor amplifier output signal and generating a first detector output signal; and (i) a second input power system generating a second system input signal and generating said third input signal to said third connector of said metal element;

(j) a second power transmitter amplifier having a second power transmitter input receiving a second system input signal and having a second power transmitter output generating a second excitation output, (k) a third resistor for interconnecting said second power transmitter output and said first connector of said coated section of said metal element so as to constitute a first path of said second excitation output signal from said second power transmitter output through said third resistor and said coated section of said metal element to said third connector of said metal element, said second excitation output signal inducing, in cooperation with said first excitation output signal, said first metal element voltage across said coated section of said metal element;

(l) a fourth resistor for interconnecting said second power transmitter output and said second connector of said non-coated section of said metal element so as to constitute a second path of said second excitation output signal from said second power transmitter output through said fourth resistor and said non-coated section of said metal element to said third connector of said metal element, said second excitation output signal further inducing, in cooperation with said first excitation output signal, said second metal clement voltage across said non-coated section of said metal clement;

(m) a second sensor amplifier having a third sensor amplifier input connected to said first connector of said coated section of said metal element, having a fourth sensor amplifier input connected to said third connector of said metal clement, and having a second sensor amplifier output generating a second sensor output signal constituted by an amplification of said first metal element voltage;

(n) a second detector having a second detector input receiving said second sensor output signal from said second sensor amplifier output, performing a conversion of said second sensor amplifier output, and generating a second detector output signal; and (o) a temperature compensating feedback circuit for compensating temperature induced variations in said first and second resistance of said metal element and utilizing said second detector output in controlling the amplitude of said first system input signal and said second system input signal so as to decrease said first system input signal and said second system input signal when said first resistance increases and so as to increase said first system input signal and said second system input signal when said first resistance decreases;

wherein said temperature compensating feedback circuit comprises:

an oscillator providing a clack pulse signal;

a reference potentiometer connected to said DC supply voltage and generating a reference voltage output signal;

a comparator having an inverting comparator input connected to said second detector output, a non-inverting comparator input connected to said reference voltage output, and having a comparator output generating a comparator output signal constituted by a positive output voltage or a negative output voltage relative to the polarity of voltage difference between said inverting comparator input and said non-inverting comparator input;

a counter having a counter clock input receiving said clock pulse signal, having a counter input receiving said comparator output signal, and having a digital counter output generating a counter output digital number, said counter output digital number being increased when receiving a clock pulse signal and receiving said comparator output signal having a positive output voltage, or said counter output digital number being reduced when receiving a clock pulse signal and receiving said comparator output signal having a negative output voltage;

a first digital ladder having a first digital input connected to said digital counter output and having a first analogue input receiving said first system input signal, said first digital ladder performing a conversion of said counter output digital number to a required amplitude of said first system input signal and generating said first system input signal having an amplitude in accordance with said counter output digital number;

a second digital ladder having a second digital input connected to said digital counter output and having a second analogue input receiving said second system input signal, said second digital ladder performing a conversion of said counter output digital number to said required amplitude of said second system input signal and generating said second system input signal having said amplitude in accordance with said counter output digital number;

and at least one of:

(1) a discriminating circuit having a detector unit measuring said first system input signal and generating a DC detector output, and having a discriminator meter comparing said DC detector output with a fixed reference voltage defined by a voltage divider and said discriminator meter displaying a voltage difference defined between said DC detector output and said fixed reference voltage so as to provide balancing information of said apparatus and enable balancing by adjusting said reference potentiometer, and (2) a discriminating circuit having a detector unit measuring said second system input signal and generating a DC detector output, and having to a discriminator meter comparing said DC detector output with a fixed reference voltage defined by a voltage divider and said discriminator meter displaying a voltage difference defined between said DC detector output and said fixed reference voltage so as to provide balancing information of said apparatus and enable balancing by adjusting said reference potentiometer.

13. The apparatus according to claim 12, further comprising:

(p) a first phase detective means connected to said first sensor amplifier output and performing a phase selective conversion of said first sensor amplifier output signal to a first real vector component voltage and a first imaginary vector component voltage of said voltage difference between said second metal element voltage and said first metal element voltage having said first frequency;

(q) a third sensor amplifier having a fifth sensor amplifier input connected to said second connector of said non-coated section of said metal element, having a sixth sensor amplifier input connected to said third connector of said metal element, and having a third sensor amplifier output generating a third sensor output signal constituted by an amplification of said part of said second metal element voltage having said second frequency;

(r) a second phase detective means connected to said third sensor amplifier output and performing a phase selective conversion of said third sensor amplifier output signal to second real vector component voltage arid a second imaginary vector component voltage of said second metal element voltage having said second frequency;

(s) a real vector component balancing circuit having a real vector component balancing circuit output generating a real balancing output signal and a real vector component balancing circuit input receiving said first system input signal, (t) a third power transmitter amplifier having third power transmitter input connected to said real vector component balancing circuit output and having a third power transmitter output connected to said first connector on said coated section of said metal element and generating a third power transmitter output signal for balancing of said first real vector component voltage;

(u) an imaginary vector component balancing circuit hiving an imaginary vector component balancing circuit output generating an imaginary balancing output signal and an imaginary vector component balancing circuit input receiving said first system input signal phase shifted by 90° and 270°; and (v) a fourth power transmitter amplifier having fourth power transmitter input connected to said imaginary vector component balancing circuit output and having a fourth power transmitter output connected to said first connector on said coated section of said metal element and generating a fourth power transmitter output signal for balancing of said first imaginary vector component voltage.

14. The apparatus according to claim 12, wherein said conversion of said first sensor amplifier output signal performed by said first detector is performed by converting said alternating first sensor amplifier output signal into a first DC voltage signal in the range of about −24V to about +24V; and wherein said conversion of said second sensor output signal performed by said second detector is performed by converting said alternating second sensor output signal into a second DC voltage signal in the range of about −24V to about +24V.

15. The apparatus according to claim 12, wherein said first and second resistances of said metal element are in a range from about 4 $\mu\Omega$ to about 4 K$\Omega$.

16. A method for measuring accumulated and instant rate of material loss or material gain and comprising:

(a) providing an apparatus comprising:

(i) a DC supply defining a positive DC voltage and a negative DC voltage;

(ii) a metal element defining a coated section having a first connector, a non-coated section having a second connector, and an interface having a third connector, said interface providing electrical and thermal connection between said coated section and said non-coated section experiencing corrosion or metal deposition in a measurement environment;

(iii) a first input power system having a first power output;

(iv) a first power transmitter amplifier having a first power transmitter input receiving said first system input signal and having a first power transmitter output;

(v) a first resistor for interconnecting said first power transmitter output and said first connector of said coated section of said metal element so as to constitute a first path of said first excitation output signal from said first power transmitter output through said first resistor and said coated section of said metal element to said third connector of said metal element;

(vi) a second resistor for interconnecting said first power transmitter output and said second connector of said non-coated section of said metal element so as to constitute a second path of said first excitation output signal from said first power transmitter output through said second resistor and said non-coated section of said metal element to said third connector of said metal element; and (vii) a first sensor amplifier having a first sensor amplifier input connected to said first connector of said coated section of said metal element, having a second sensor amplifier input connected to said second connector of said non-coated section of said metal element, and having a first sensor output;

(b) supplying said apparatus with power to perform measuring operations;

(c) generating a first system input signal and generating an interface input signal to said third connector of said metal element;

(d) generating a first excitation output signal on said first power transmitter output;

(e) inducing a first metal element voltage across said coated section of said metal element by means of said first excitation output signal;

(f) inducing a second metal element voltage across said non-coated section of said metal element by means of said first excitation output signal;

(g) generating a first sensor amplifier output signal by amplifying said first metal element voltage, said second metal element voltage and/or a voltage difference between said second metal element voltage and said first metal element voltage by means of said first sensor output;

(h) defining a first resistance between said first connector of said coated section and said third connector of said metal element and a second resistance between said second connector of said non-coated section and said third connector of said metal element; and (i) determining either the increase of said second resistance as a function of corrosion or tho decrease of said second resistance as a function of metal deposition, so as to induce said voltage difference between said second moral element voltage and said first metal element voltage and to determine corrosion of or metal deposition of said metal element from the increase or decrease of said second resistance.

* * * * *